United States Patent
Cohen et al.

(10) Patent No.: US 8,116,881 B2
(45) Date of Patent: *Feb. 14, 2012

(54) ELECTRODE ASSEMBLY FOR NERVE CONTROL

(75) Inventors: Ehud Cohen, Ganei Tikva (IL); Tamir Ben-David, Tel Aviv (IL); Shai Ayal, Jerusalem (IL); Omry Ben-Ezra, Tel Aviv (IL)

(73) Assignee: Bio Control Medical (B.C.M.) Ltd, Yehud (IL)

( * ) Notice: Subject to any disclaimer, the term of this patent is extended or adjusted under 35 U.S.C. 154(b) by 965 days.

This patent is subject to a terminal disclaimer.

(21) Appl. No.: 11/978,776

(22) Filed: Oct. 29, 2007

(65) Prior Publication Data
US 2008/0132983 A1    Jun. 5, 2008

Related U.S. Application Data

(63) Continuation-in-part of application No. 11/022,011, filed on Dec. 22, 2004, now Pat. No. 7,561,922, which is a continuation-in-part of application No. 10/866,601, filed on Jun. 10, 2004, now abandoned.

(51) Int. Cl.
*A61N 1/05* (2006.01)
(52) U.S. Cl. .................................................. 607/118
(58) Field of Classification Search ............ 607/118
See application file for complete search history.

(56) References Cited

U.S. PATENT DOCUMENTS

| 4,026,300 A | 5/1977 | DeLuca et al. |
| 4,535,785 A | 8/1985 | Van Den Honert et al. |
| 4,573,481 A | 3/1986 | Bullara |
| 4,602,624 A | 7/1986 | Naples et al. |
| 4,608,985 A | 9/1986 | Crish et al. |
| 4,628,942 A | 12/1986 | Sweeney et al. |
| 4,649,936 A | 3/1987 | Ungar et al. |
| 5,199,430 A | 4/1993 | Fang et al. |
| 5,215,086 A | 6/1993 | Terry et al. |

(Continued)

FOREIGN PATENT DOCUMENTS

DE    198 47 446    4/2000

(Continued)

OTHER PUBLICATIONS

Office Action, issued Oct. 24, 2008, in connection with U.S. Appl. No. 11/022,011, filed Dec. 22, 2004.

(Continued)

*Primary Examiner* — George Evanisko
(74) *Attorney, Agent, or Firm* — Sughrue Mion, PLLC

(57) ABSTRACT

Apparatus is provided for applying current to a nerve, including a housing, configured to be placed in a vicinity of the nerve. At least one electrode is fixed to the housing such that the at least one electrode does not come in direct physical contact with the nerve when the housing is placed in the vicinity of the nerve, and such that the electrode surrounds greater than 180 degrees of a circumference of the nerve after the placement of the housing. Two end insulating elements are fixed to the housing such that the at least one electrode is between the end insulating elements, and the end insulating elements come in contact or practically in contact with the nerve when the housing is placed in the vicinity of the nerve. Other embodiments are also described.

4 Claims, 18 Drawing Sheets

U.S. PATENT DOCUMENTS

| | | | |
|---|---|---|---|
| 5,215,089 A | | 6/1993 | Baker, Jr. |
| 5,282,468 A | | 2/1994 | Klepinski |
| 5,400,784 A | * | 3/1995 | Durand et al. ............... 600/377 |
| 5,423,872 A | | 6/1995 | Cigaina et al. |
| 5,487,756 A | | 1/1996 | Kallesoe et al. |
| 5,505,201 A | | 4/1996 | Grill et al. |
| 5,634,462 A | | 6/1997 | Tyler et al. |
| 5,755,750 A | | 5/1998 | Petruska et al. |
| 5,824,027 A | * | 10/1998 | Hoffer et al. .................. 607/118 |
| 5,833,664 A | | 11/1998 | Seare, Jr. |
| 5,938,596 A | | 8/1999 | Woloszko et al. |
| 6,230,061 B1 | | 5/2001 | Hartung |
| 6,341,236 B1 | | 1/2002 | Osorio et al. |
| 6,456,866 B1 | | 9/2002 | Tyler et al. |
| 6,600,954 B2 | | 7/2003 | Cohen et al. |
| 6,600,956 B2 | | 7/2003 | Maschino et al. |
| 6,684,105 B2 | | 1/2004 | Cohen et al. |
| 6,907,295 B2 | | 6/2005 | Gross et al. |
| 7,218,971 B2 | | 5/2007 | Heil, Jr. et al. |
| 7,403,819 B1 | | 7/2008 | Shelchuk et al. |
| 7,765,000 B2 | | 7/2010 | Zhang et al. |
| 2003/0040785 A1 | * | 2/2003 | Maschino et al. ............ 607/118 |
| 2003/0045909 A1 | | 3/2003 | Gross et al. |
| 2003/0050677 A1 | * | 3/2003 | Gross et al. ..................... 607/72 |
| 2005/0038490 A1 | | 2/2005 | Gross et al. |
| 2005/0065553 A1 | | 3/2005 | Ben Ezea et al. |
| 2006/0030919 A1 | | 2/2006 | Mrva et al. |
| 2006/0136024 A1 | | 6/2006 | Cohen et al. |
| 2006/0195170 A1 | | 8/2006 | Cohen et al. |
| 2006/0282145 A1 | | 12/2006 | Caparso et al. |
| 2008/0132983 A1 | | 6/2008 | Cohen et al. |

FOREIGN PATENT DOCUMENTS

| | | |
|---|---|---|
| EP | 0 688 577 | 12/1995 |
| EP | 0 865 800 | 9/1998 |
| EP | 1 785 160 | 5/2007 |
| WO | 01/10375 | 2/2001 |
| WO | WO 2001/10357 | 2/2001 |
| WO | 03/018113 | 3/2003 |
| WO | 03/099373 | 12/2003 |
| WO | WO 2008/007360 | 1/2008 |

OTHER PUBLICATIONS

Supplementary European Search Report, issued Nov. 4, 2009, in connection with European Patent Application No. 03723040.6, filed May 23, 2003.

European Search Report, issued Aug. 27, 2009, in connection with European Patent Application No. 09251749.9.

Office Action, issued Dec. 8, 2009, in connection with U.S. Appl. No. 11/347,120, filed Feb. 2, 2006.

Sweeney, J.D., et al. "An asymmetric two electrode cuff for generation of unidirectionally propagated action potentials," *IEEE Transactions an Biomedical Engineering*, vol. BME-33 (6) (1986).

Office Action, issued Apr. 28, 2010, in connection with U.S. Appl. No. 11/981,301, filed Oct. 30, 2007.

Office Action, issued Apr. 15, 2009, in connection with U.S. Appl. No. 11/347,120, filed Feb. 2, 2006.

Beratta, R. et al., (1989) "Orderly stimulation of skeletal muscle motor units with tripolar nerve cuff electrode." *IEEE Transactions on Biomedical Engineering*: vol. 36(8): 836-843.

Deurloo, K.E. et al., (1998) "Transverse tripolar stimulation of peripheral nerve: a modeling study of spatial selectivity." *Medical & Biological Engineering & Computing*: vol. 36(1): 66-74.

Goodall, E.V. et al., (1996) "Position-selective activation of peripheral nerve fibers with a cuff electrode." *IEEE Transactions on Biomedical Engineering*: vol. 43(8): 851-856.

Grill, W.M. et al., (1997) "Inversion of the current-distance relationship by transient depolarization." *IEEE Transactions on Biomedical Engineering*: vol. 44(1): 1-9.

Mushahwar, V.K. et al., (2000) "Muscle recruitment through electrical stimulation of the lumbo-sacral spinal cord." *IEEE Transactions on Biomedical Engineering*: vol. 8(1): 22-29.

Naples, G.G. et al., (1988) "A spiral nerve cuff electrode for peripheral nerve stimulation." *IEEE Transactions on Biomedical Engineering*: vol. 35(11): 905-916.

Office Action issued May 18, 2007 during the prosecution of Applicants' U.S. Appl. No. 10/529,149.

Office Action issued Sep. 14, 2007 during the prosecution of Applicants' U.S. Appl. No. 10/529,149.

Rijkhoff, N.J. et al., (1994) "Acute animal studies on the use of anodal block to reduce urethral resistance in sacral root stimulation." *IEEE Transactions on Rehabilitation Engineering*: vol. 2(2): 92-99.

Rijkhoff, N.J. et al., (1998) "Orderly recruitment of motoneurons in an acute rabbit model." *Proc. of the Annual Conf. of the IEEE Engineering in Medicine and Biology Society*: vol. 20(5): 2564-2565.

Rijkhoff, N.J. et al., (1999) "Selective stimulation of small diameter nerve fibers in a mixed bundle." *Proc. of the Annual project meeting sensations/neuros and Mid-Term Review Meeting on the TMR-Network Neuros*: Apr. 21-23, 1999: 20-21.

Sweeney, J.D. et al., (1990) "An asymmetric two electrode cuff for generation of unidirectionally propagated action potentials." *IEEE Transactions on Biomedical Engineering*: vol. BME-33(6): 541-549.

Sweeney, J.D. et al., (1986) "A nerve cuff technique for selective excitation of peripheral nerve trunk regions." *IEEE Transactions on Biomedical Engineering*: vol. 37(7): 706-715.

Tarver, W.B. et al., (1992) "Clinical experience with a helical bipolar stimulating lead." *Pace*: vol. 15, October, Part II: 1545-1556.

Ungar, I.J. et al., (1986) "Generation of unidirectionally propagating action potentials using a monopolar electrode cuff." *Annals of Biomedical Engineering*: 14: 437-450.

U.S. Appl. No. 60/383,157, filed May 23, 2002 (Ayal, S. et al.).

Van Den Honert, C. et al., (1981) "A technique for collision block of peripheral nerve: Frequency dependence." *MP-12, IEEE Transactions on Biomedical Engineering*: vol. 28: 379-382.

Van Den Honert, C. et al., (1979) "Generation of unidirectionally propagated action potentials in a peripheral nerve by brief stimuli." *Science*: vol. 206: 1311-1312.

Veraart, C. et al., (1993) "Selective control of muscle activation with a multipolar nerve cuff electrode." *IEEE Transactions on Biomedical Engineering*: vol. 40(7): 640-653.

An Official Action dated Feb. 4, 2011, which issued during the prosecution of Applicant's U.S. Appl. No. 11/974,951.

\* cited by examiner

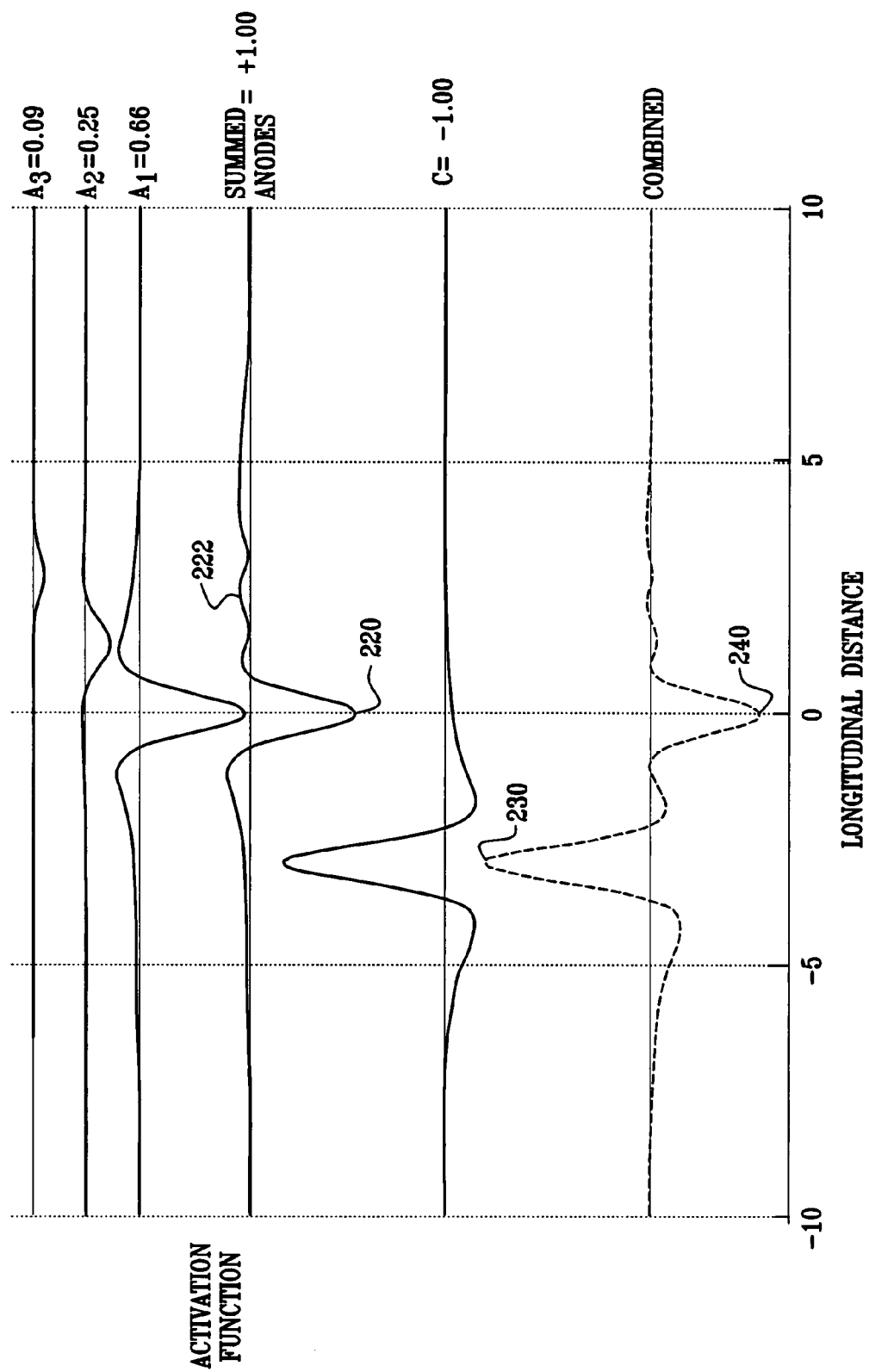

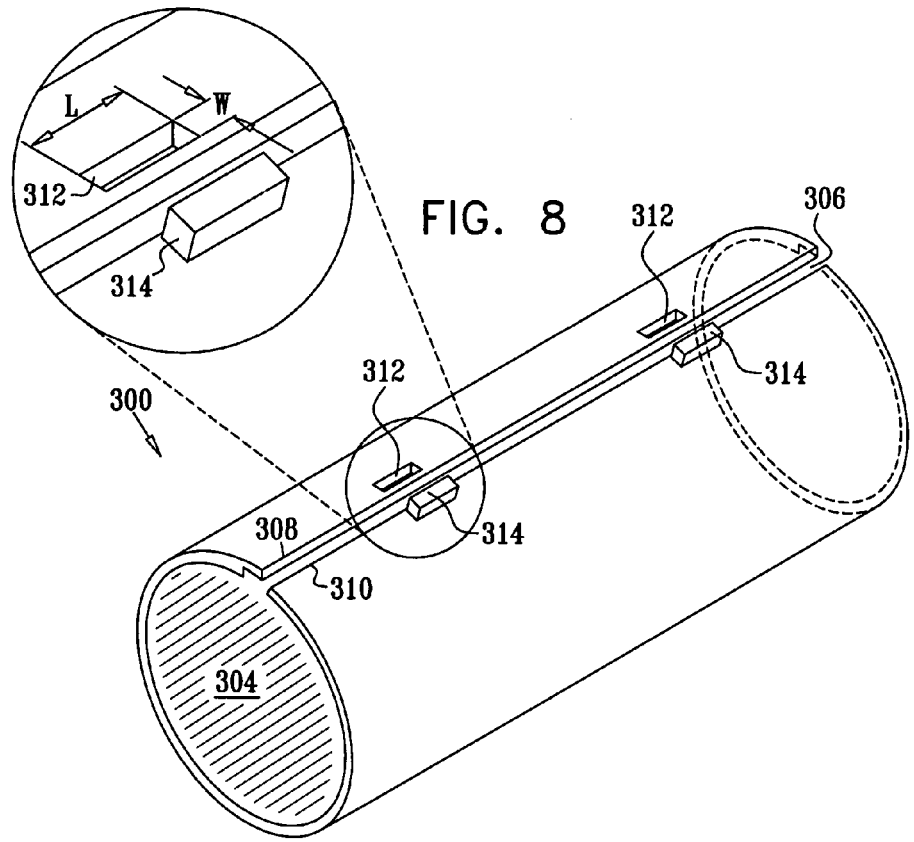
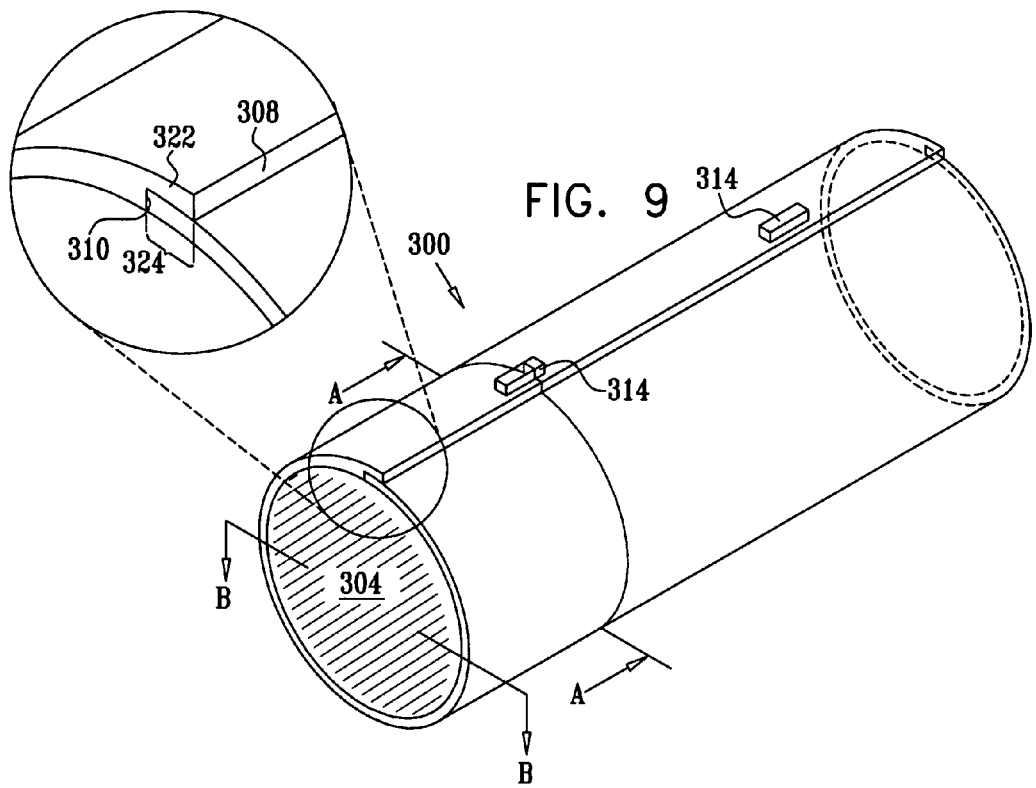

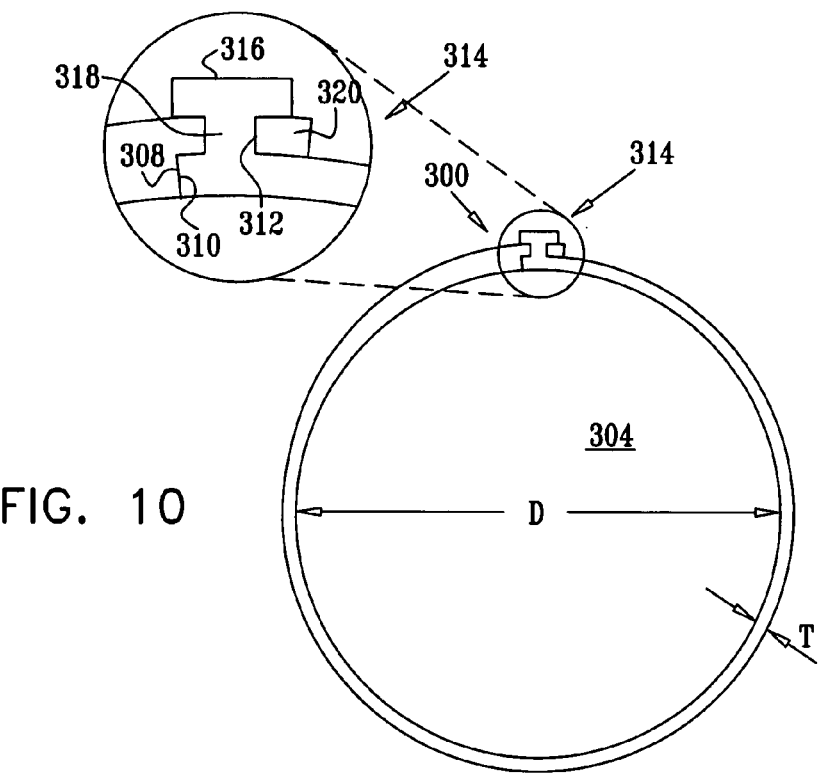
FIG. 10
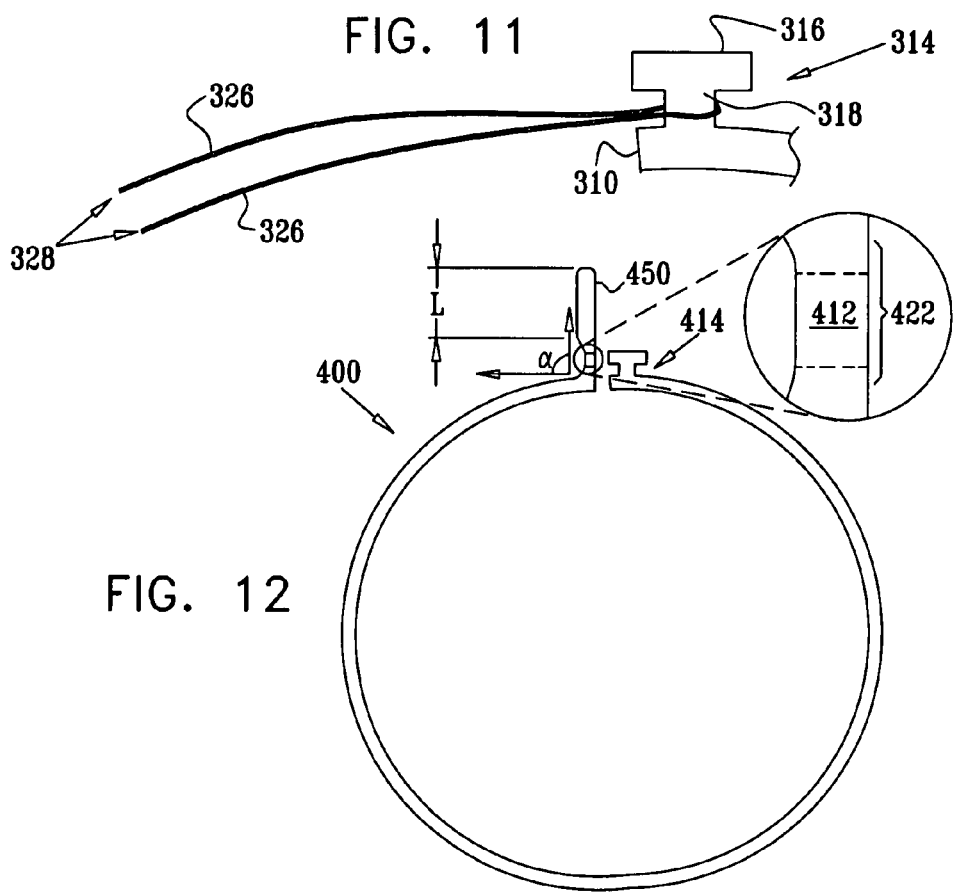
FIG. 11
FIG. 12

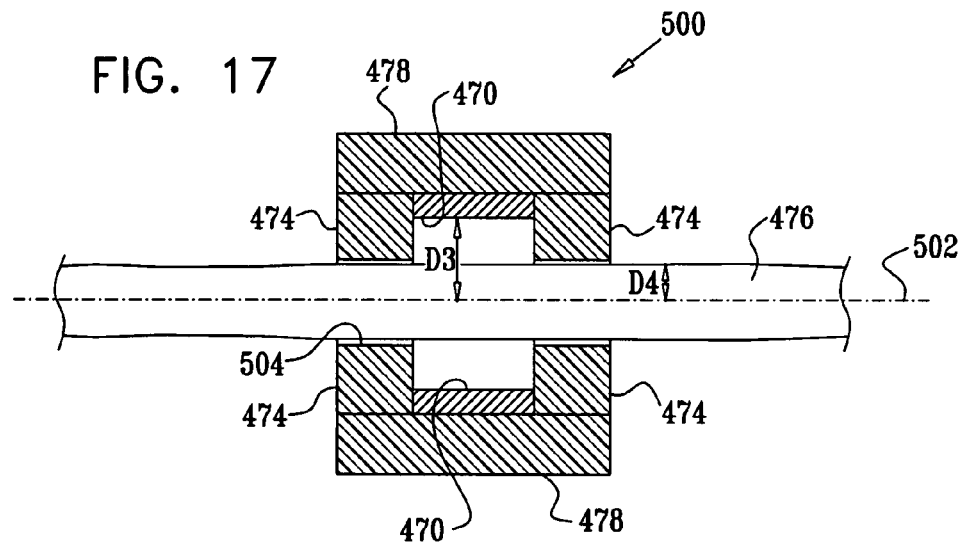
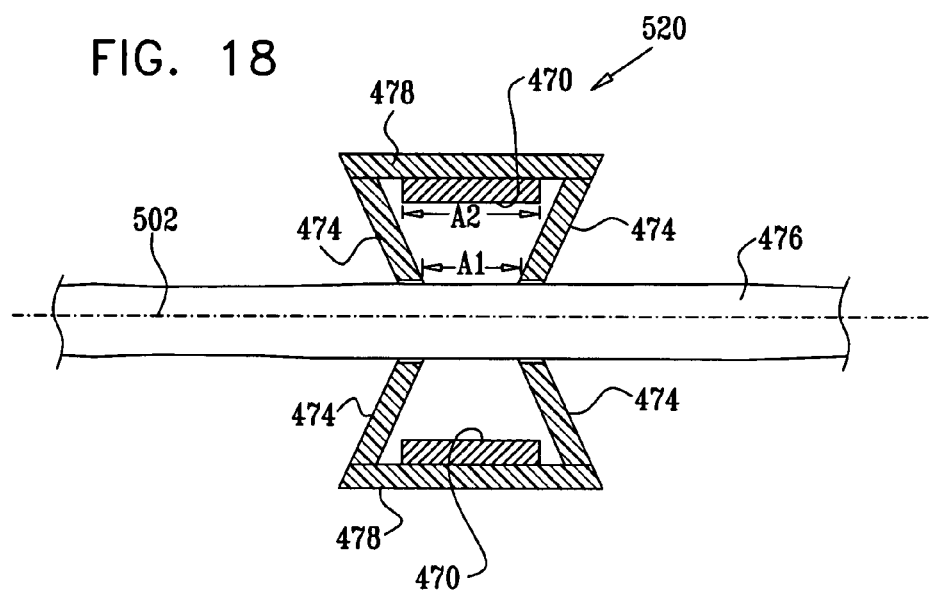

ELECTRODE ASSEMBLY FOR NERVE CONTROL

CROSS-REFERENCES TO RELATED APPLICATIONS

The present patent application is a continuation-in-part of: (a) U.S. patent application Ser. No. 11/022,011, filed Dec. 22, 2004, now U.S. Pat. No. 7,561,922, and (b) U.S. patent application Ser. No. 10/866,601, filed Jun. 10, 2004, now abandoned. Both of the above-mentioned patent applications are assigned to the assignee of the present patent application and are incorporated herein by reference.

FIELD OF THE INVENTION

The present invention relates generally to electrical stimulation of tissue, and specifically to methods and devices for regulating the stimulation of nerves.

BACKGROUND OF THE INVENTION

As defined by Rattay, in the article, "Analysis of models for extracellular fiber stimulation," IEEE Transactions on Biomedical Engineering, Vol. 36, no. 2, p. 676, 1989, which is incorporated herein by reference, the activation function (AF) is the second spatial derivative of the electric potential along an axon. In the region where the activation function is positive, the axon depolarizes, and in the region where the activation function is negative, the axon hyperpolarizes. If the activation function is sufficiently positive, then the depolarization will cause the axon to generate an action potential; similarly, if the activation function is sufficiently negative, then local blocking of action potentials transmission occurs. The activation function depends on the current applied, as well as the geometry of the electrodes and of the axon.

For a given electrode geometry, the equation governing the electrical potential is:

$$\nabla(\sigma \nabla U) = 4\pi j,$$

where U is the potential, $\sigma$ is the conductance tensor specifying the conductance of the various materials (electrode housing, axon, intracellular fluid, etc.), and j is a scalar function representing the current source density specifying the locations of current injection. The activation function is found by solving this partial differential equation for U. If the axon is defined to lie in the z direction, then the activation function is:

$$AF = \frac{\partial^2 U}{\partial z^2}.$$

In a simple, illustrative example of a point electrode located a distance d from the axis of an axon in a uniformly-conducting medium with conductance $\sigma$, the two equations above are solvable analytically, to yield:

$$AF = \frac{I_{el}}{4\pi\sigma} \cdot \frac{2z^2 - d^2}{(z^2 + d^2)^{2.5}},$$

where $I_{el}$ is the electrode current. It is seen that when $\sigma$ and d are held constant, and for a constant positive $I_{el}$ (to correspond to anodal current), the minimum value of the activation function is negative, and is attained at z=0, i.e., at the point on the nerve closest to the source of the anodal current. Thus, the most negative point on the activation function corresponds to the place on a nerve where hyperpolarization is maximized, namely at the point on the nerve closest to the anode.

Additionally, this equation predicts positive "lobes" for the activation function on either side of z=0, these positive lobes peaking in their values at a distance which is dependent on each of the other parameters in the equation. The positive values of the activation function correspond to areas of depolarization, a phenomenon typically associated with cathodic current, not anodal current. However, it has been shown that excess anodal current does indeed cause the generation of action potentials adjacent to the point on a nerve corresponding to z=0, and this phenomenon is therefore called the "virtual cathode effect." (An analogous, but reverse phenomenon, the "virtual anode effect" exists responsive to excess cathodic stimulation.)

U.S. Pat. No. 6,684,105 to Cohen et al., which is assigned to the assignee of the present application and is incorporated herein by reference, describes apparatus comprising an electrode device adapted to be coupled to longitudinal nervous tissue of a subject, and a control unit adapted to drive the electrode device to apply to the nervous tissue a current which is capable of inducing action potentials that propagate in the nervous tissue in a first direction, so as to treat a condition. The control unit is further adapted to suppress action potentials from propagating in the nervous tissue in a second direction opposite to the first direction.

U.S. Pat. No. 6,230,061 to Hartung, which is incorporated herein by reference, describes an electrode arrangement for stimulating the heart by means of: (a) an implantable cardiac pacemaker, (b) a first electrode, coupled to a first output of the pacemaker via an intracardiac electrode line, and (c) a second electrode, for transmitting electrical stimulation pulses to the heart tissue, coupled to a second output of the pacemaker via the electrode line. The voltage pulses at the two electrodes have differing polarities relative to a third electrode. The first and second electrodes are arranged on the electrode line in such a way that the electrical dipole field which forms is distorted towards the stimulation point in such a way that a raised gradient above the stimulus threshold is formed there.

A number of patents and articles describe methods and devices for stimulating nerves to achieve a desired effect. Often these techniques include a design for an electrode or electrode cuff.

U.S. Pat. Nos. 4,608,985 to Crish et al. and 4,649,936 to Ungar et al., which are incorporated herein by reference, describe electrode cuffs for selectively blocking orthodromic action potentials passing along a nerve trunk, in a manner intended to avoid causing nerve damage.

PCT Patent Publication WO 01/10375 to Felsen et al., which is incorporated herein by reference, describes apparatus for modifying the electrical behavior of nervous tissue. Electrical energy is applied with an electrode to a nerve in order to selectively inhibit propagation of an action potential.

U.S. Pat. No. 5,755,750 to Petruska et al., which is incorporated herein by reference, describes techniques for selectively blocking different size fibers of a nerve by applying direct electric current between an anode and a cathode that is larger than the anode.

U.S. Pat. No. 5,487,756 to Kallesoe et al., which is incorporated herein by reference, describes an implantable cuff having a closure comprising a set of small interdigitated tubes lying along the edges of a longitudinal slit opening in the cuff. A rod-like locking member is inserted through the interdigitated tubes to lock the cuff closed. A flexible flap attached to the inside of the cuff is described as electrically and mechanically isolating the interior of the cuff from the exterior.

U.S. Pat. No. 5,824,027 Hoffer et al., which is incorporated herein by reference, describes a nerve cuff having one or more sets of electrodes for selectively recording electrical activity in a nerve or for selectively stimulating regions of the nerve. Each set of electrodes is located in a longitudinally-extending chamber between a pair of longitudinal ridges which project into the bore of the nerve cuff. The ridges are electrically insulating and serve to improve the selectivity of the nerve cuff. The ridges seal against an outer surface of the nerve without penetrating the nerve. In an embodiment, circumferential end sealing ridges extend around the bore at each end of the longitudinal ridges, and are described as enhancing the electrical and/or fluid isolation between different ones of the longitudinally-extending chambers.

U.S. Pat. No. 4,628,942 to Sweeney et al., which is incorporated herein by reference, describes an annular electrode cuff positioned around a nerve trunk for imposing electrical signals on to the nerve trunk for the purpose of generating unidirectionally propagated action potentials. The electrode cuff includes an annular cathode having a circular passage therethrough of a first diameter. An annular anode has a larger circular passage therethrough of a second diameter, which second diameter is about 1.2 to 3.0 times the first diameter. A non-conductive sheath extends around the anode, cathode, and nerve trunk. The anode and cathode are placed asymmetrically to one side of the non-conductive sheath.

U.S. Pat. No. 5,634,462 to Tyler et al., which is incorporated herein by reference, describes a corrugated sheet of non-conductive biocompatible material that is biased to circumferentially contract around a nerve or other body tissue. Conductive members are disposed on inwardly projecting portions of the corrugated sheet formed into a cylinder around the nerve. The conductive segments are electrically conductive for applying or recording electrical impulses or fluid conductive for infusing medications or draining fluids from the nerve. The corrugated sheet, when wrapped around a nerve, is self-biased to slowly controllably contract to its original size.

U.S. Pat. No. 6,456,866 to Tyler et al., which is incorporated herein by reference, describes a flat interface nerve electrode having a plurality of conductive elements embedded in a non-conductive cuff structure, which acts to gently and non-evasively redefine the geometry of a nerve through the application of a force so as to apply pressure to a nerve in a defined range.

U.S. Pat. No. 4,602,624 to Naples et al., which is incorporated herein by reference, describes a self-curling sheet of non-conductive material that is biased to curl into a tight spiral. A cut out is removed from one corner of the sheet such that, when the sheet spirals, a passage defined axially therethrough has one portion with a smaller diameter and another portion with a larger diameter. A pair of conductive strips are disposed on the self-curling sheet such that one extends peripherally around each of the larger and smaller diameter regions of the passage therethrough. The conductive segments may be electrically conductive for applying electrical impulses or fluid conductive for infusing medications. In use, a first edge of the self-curling sheet is disposed adjacent a nerve trunk which is to receive the cuff therearound. The self-curling sheet is controllably permitted to curl around the nerve forming an annular cuff therearound.

U.S. Pat. No. 6,600,956 to Maschino et al., which is incorporated herein by reference, describes an electrode assembly to be installed on a patient's nerve. The assembly has a thin, flexible, electrically insulating circumneural carrier with a split circumferential configuration longitudinally attached to a lead at the distal end thereof. The carrier possesses circumferential resiliency and has at least one flexible, elastic electrode secured to the underside thereof and electrically connected to an electrical conductor in said lead. A fastener serves to close the split configuration of the carrier to prevent separation from the nerve after installation of the electrode assembly onto the nerve. Tear-away webbing secured to adjacent serpentine segments of the lead near the carrier enables the lead to lengthen with patient movements.

U.S. Pat. No. 5,199,430 to Fang et al., which is incorporated herein by reference, describes cuff electrodes that are implanted around sacral ventral root nerve trunks.

U.S. Pat. No. 5,423,872 to Cigaina, which is incorporated herein by reference, describes a process for treating obesity and syndromes related to motor disorders of the stomach of a patient. The process consists of artificially altering, by means of sequential electrical pulses and for preset periods of time, the natural gastric motility of the patient to prevent emptying or to slow down gastric transit. The '872 patent describes an electrocatheter adapted to be coupled to a portion of the stomach. A portion of the electrocatheter has a rough surface for producing a fibrous reaction of the gastric serosa, in order to contribute to the firmness of the anchoring.

U.S. Pat. No. 5,282,468 to Klepinski, which is incorporated herein by reference, describes an implantable neural electrode.

U.S. Pat. No. 4,535,785 to van den Honert et al., which is incorporated herein by reference, describes implantable electronic apparatus.

U.S. Pat. No. 5,215,086 to Terry et al., which is incorporated herein by reference, describes a method for applying electrical stimulation to treat migraine headaches.

U.S. Pat. No. 4,573,481 to Bullara, which is incorporated herein by reference, describes an implantable helical electrode assembly, configured to fit around a nerve, for electrically triggering or measuring an action potential or for blocking conduction in nerve tissue. A tissue-contacting surface of each electrode is roughened to increase the electrode surface area.

U.S. Pat. No. 6,341,236 to Osorio et al., which is incorporated herein by reference, describes techniques for electrically stimulating the vagus nerve to treat epilepsy with minimized or no effect on the heart. Treatment is carried out by an implantable signal generator, one or more implantable electrodes for electrically stimulating a predetermined stimulation site of the vagus nerve, and a sensor for sensing characteristics of the heart such as a heart rate. The heart rate information from the sensor can be used to determine whether the vagus nerve stimulation is adversely affecting the heart. Once threshold parameters are met, the vagus nerve stimulation may be stopped or adjusted. In an alternative embodiment, a modified pacemaker is used to maintain the heart in desired conditions during the vagus nerve stimulation. In yet another embodiment, a modified pacemaker having circuitry that determines whether a vagus nerve is being stimulated is used. In the event that the vagus nerve is being stimulated, the modified pacemaker may control the heart to maintain it within desired conditions during the vagus nerve stimulation.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33(6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

Hoffer J A et al., "How to use nerve cuffs to stimulate, record or modulate neural activity," in *Neural Prostheses for Restoration of Sensory and Motor Function*, Chapin J K et al. (Eds.), CRC Press (1st edition, 2000)

In physiological muscle contraction, nerve fibers are recruited in the order of increasing size, from smaller-diameter fibers to progressively larger-diameter fibers. In contrast, artificial electrical stimulation of nerves using standard techniques recruits fibers in a larger- to smaller-diameter order, because larger-diameter fibers have a lower excitation threshold. This unnatural recruitment order causes muscle fatigue and poor force gradation. Techniques have been explored to mimic the natural order of recruitment when performing artificial stimulation of nerves to stimulate muscles.

Fitzpatrick et al., in "A nerve cuff design for the selective activation and blocking of myelinated nerve fibers," Ann. Conf. of the IEEE Eng. in Medicine and Biology Soc, 13(2), 906 (1991), which is incorporated herein by reference, describe a tripolar electrode used for muscle control. The electrode includes a central cathode flanked on its opposite sides by two anodes. The central cathode generates action potentials in the motor nerve fiber by cathodic stimulation. One of the anodes produces a complete anodal block in one direction so that the action potential produced by the cathode is unidirectional. The other anode produces a selective anodal block to permit passage of the action potential in the opposite direction through selected motor nerve fibers to produce the desired muscle stimulation or suppression.

The following articles, which are incorporated herein by reference, may be of interest:

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

The following articles, which are incorporated herein by reference, describe techniques using point electrodes to selectively excite peripheral nerve fibers distant from an electrode without exciting nerve fibers close to the electrode:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

SUMMARY OF THE INVENTION

In some embodiments of the present invention, an electrode assembly for applying current to a nerve comprises a cathode, a primary inhibiting anode and a secondary inhibiting anode, which are fixed within a housing. The cathode, near one end of the housing, is placed on or near the nerve, over a "cathodic longitudinal site" of the nerve, and is driven by a control unit to apply a cathodic current to the nerve. The primary inhibiting anode, adjacent to the cathode in the housing, is placed on or over a "primary anodal longitudinal site" of the nerve, and is driven to apply a primary anodal current to the nerve. The secondary inhibiting anode, which is separated from the cathode by the primary inhibiting anode, is placed on or over a "secondary anodal longitudinal site" of the nerve, and applies a secondary anodal current to the nerve.

Typically, the cathodic current applied at the cathodic longitudinal site stimulates fibers within the nerve to generate action potentials which travel in both directions within the nerve—i.e., towards the anodes ("the anodal direction"), and in the opposite direction, out of the housing, towards a target ("the target direction"). The anodal current, by contrast, is typically applied so as to inhibit the action potentials which were generated at the cathodic longitudinal site and which subsequently traveled in the anodal direction.

For most applications, the secondary anodal current is of lower magnitude than the primary anodal current. In this manner, the "virtual cathode" effect induced by the primary anodal current is minimized. As described in the Background section of the present patent application, the virtual cathode effect can stimulate—rather than block—the generation of action potentials in fibers in a region adjacent to the application of anodal current of a sufficiently high magnitude. In accordance with an embodiment of the present invention, application of the primary and secondary anodal currents in appropriate ratios is configured to generally minimize the virtual cathode effect. Typically, but not necessarily, the ratio of the primary to the secondary anodal current ranges from 5:1 to 10:1.

In an embodiment, a tertiary inhibiting anode is employed to reduce any virtual cathode effect which may be induced by the secondary inhibiting anode. For example, relative to a normalized cathodic current of −1, the primary inhibiting anode, secondary inhibiting anode, and tertiary inhibiting anode may be configured to apply respective currents of 0.66, 0.25, and 0.09. For some applications, the various anodes are independently driven by a control unit, so as to optimize the minimization of the virtual cathode effect and the maximization (when appropriate) of the anodally-induced hyperpolarization. Alternatively, fixed ratios are pre-defined for the currents applied by the anodes, and are set in hardware, e.g., by a set of resistors which link a single lead coming from the control unit to the respective anodes.

In an embodiment, an elongated anode replaces the anodes described hereinabove. The elongated anode, when placed on or over a nerve, typically has at least two levels of electrical impedance associated therewith, between respective sites on the elongated anode and the nerve. For some applications, the portion of the elongated anode nearest the cathode has a lower level of impedance to the nerve than does another portion of the elongated anode, further from the cathode. For some applications, the variation in impedance is achieved by applying a coating (e.g., IrO2 or a more resistive material) in progressively increasing thickness to the elongated anode, beginning with a low level of the coating at the end of the elongated anode near the cathode. Alternatively or additionally, the geometry of the elongated anode is configured so as to effect the change in impedance as described. It is noted that the impedance between any site on the elongated anode and the nerve is a function not only of the properties of the anode itself, but also of the biological material which naturally permeates the region between the nerve and the anode.

For some applications, a primary fiber-selection anode is incorporated into the housing, adjacent to the cathode and on the other side of the housing from the primary and secondary inhibiting anodes. (Thus, the sequence of electrodes in the housing is: primary fiber-selection anode, cathode, primary inhibiting anode, secondary inhibiting anode.) The primary fiber-selection anode is typically driven to apply anodal current of sufficient magnitude to block cathode-induced action potential propagation in some fibers, generally the larger fibers, which are more sensitive to the anodal current. If the current applied by the primary fiber-selection anode is not too high, then less-sensitive fibers, typically the smaller fibers in the nerve, are not blocked by the anodal current. Therefore, action potentials induced by the cathode continue to propagate in the smaller fibers, past the primary fiber-selection anode and out of the housing. By increasing the current driven through the primary fiber-selection anode, progressively smaller fibers are inhibited from propagating action potentials. Conversely, by decreasing the application of current through the primary fiber-selection anode, larger fibers are able to propagate action potentials, until, in the limit where the primary fiber-selection anode's current is zero, all fibers stimulated by the cathode convey their action potentials out of the housing and towards the target.

In an embodiment, a secondary fiber-selection anode is also incorporated into the housing, adjacent to the primary fiber-selection anode and on the far side of the cathode. (Thus, the sequence of electrodes in the housing is: secondary fiber-selection anode, primary fiber-selection anode, cathode, primary inhibiting anode, secondary inhibiting anode.) In a fashion analogous to that described hereinabove with respect to the secondary inhibiting anode, the secondary fiber-selection anode is typically driven to apply a current to the nerve smaller than that applied by the primary fiber-selection anode, so as to counteract the virtual cathode effect which would otherwise, in some circumstances, induce action potential propagation responsive to the current applied by the primary fiber-selection anode.

In some embodiments of the present invention, an electrode assembly for applying current to a nerve having a longitudinal axis comprises a housing, adapted to be placed in a vicinity of the nerve and a cathode and an anode, fixed to the housing. The cathode and anode are attached to the housing such that, when the housing is placed in the vicinity of the nerve, both the distance of the cathode and the distance of the anode to the axis are at least approximately 1.5 times the radius of the nerve. By placing the cathode and anode at such a distance, increased electrical field uniformity is obtained within the nerve. In particular, the activation function (as defined in the Background section of this application) varies only relatively little across the cross-section of the nerve. This, in turn, increases the ability of a control unit driving the cathode and anode to assure that most fibers within the nerve will experience generally the same level of applied currents.

In some embodiments of the present invention, an electrode assembly is provided for applying current to a nerve having a radius and a longitudinal central axis. The electrode assembly comprises a housing, which is placed in a vicinity of the nerve, and first and second electrodes, fixed to the housing. An insulating element is fixed to the housing between the first and second electrodes so as to define a characteristic closest "insulating element distance" to the central axis that is at least approximately 1.5 times the radius of the nerve. Typically, the electrodes are located at the same distance from the central axis or at a greater distance therefrom. In an embodiment, the face of each electrode is located at a distance from the central axis less than or equal to the closest insulating element distance plus the width (i.e., the longitudinal extent along the nerve) of the electrode. In an embodiment, the width of each electrode is approximately one half of the radius of the nerve.

Although many geometrical configurations are suitable for applying the principles of the present invention, the housings, electrodes, and insulating elements described herein are typically generally cylindrical, i.e., having circular cross-sections. Alternatively or additionally, at least some of these components are located at discrete locations with respect to the axis of the nerve (e.g., a single electrode located at "12 o'clock," or four electrodes or insulating elements may be evenly distributed around the axis).

In some embodiments of the present invention, an electrode assembly for applying current to a nerve comprises a cathode and a plurality of anodes. The cathode is placed in a vicinity of a cathodic site of the nerve, and the plurality of anodes are placed in a vicinity of respective anodal longitudinal sites of the nerve. The plurality of anodes apply respective anodal currents to the nerve, that define, in combination, an anodal activation function having a depolarization portion and a hyperpolarization portion. For many applications of the present invention, the hyperpolarization portion is the "desired" portion of the anodal activation function. For example, the hyperpolarization portion may be configured to block action potential propagation in a particular direction.

By contrast, it is desired when performing many of these applications to minimize the depolarization portion of the anodal activation function, because the location on the nerve of the depolarization portion corresponds to the location of the virtual cathode described hereinabove. If no countermeasures would be taken, the virtual cathode could be associated with an undesired stimulation of fibers in the nerve under the virtual cathode. The virtual cathode effect could be minimized to some extent by reducing the anodal current, but, if in excess, this would result in a decrease in the magnitude of the (typically desired) hyperpolarization region. If the anodal current is only minimally reduced, in order to avoid adversely decreasing the magnitude of the hyperpolarization region, then the virtual cathode effect would typically still be present. The inventors have determined that for many electrode configurations, there is no suitable balance, i.e., either the virtual cathode effect will be reduced to a desired level, or the hyperpolarization portion of the activation function will be maintained at a sufficiently high magnitude.

To address this issue, the plurality of anodes provided by these embodiments of the present invention are typically configured so as to have the maximum magnitude of the hyperpolarization portion be at least five times the maximum magnitude of the depolarization amplitude. In this manner, the desired hyperpolarization effect is preserved, and the extent of depolarization due to the anodal current is minimized. Typically, this ratio of anodally-induced hyperpolarization to depolarization is attained by using one or more of the following: (a) one or more secondary inhibiting anodes, as described hereinabove, to minimize the virtual cathode effect, (b) one or more insulating elements whose closest approach to the nerve generally remains further from the central axis of the nerve than approximately 1.5 times the radius of the nerve, or (c) electrodes, whose closest approach to the nerve generally remains further from the central axis of the nerve than approximately 1.5 times the radius of the nerve.

In some embodiments of the present invention, an electrode assembly for applying current to a nerve having a longitudinal axis, comprises two or more electrodes, adapted to be placed in a vicinity of a longitudinal site of the nerve, at respective positions around the axis. If there are only two electrodes, then the control unit typically alternates the direction of driving a current between the two electrodes at a rate greater than 1000 Hz.

When there are three or more electrodes, thereby defining a ring of electrodes, the control unit typically cycles around the electrodes in accordance with a stimulation protocol. For example, one such protocol for three electrodes may include driving current between electrodes 1 and 2, then 2 and 3, then 3 and 1, then 1 and 2, etc., cycling through the combinations at an electrode-pair transition average rate of greater than 1000 Hz, or, for some applications, greater than 10,000 Hz. For larger numbers of electrodes, e.g., 6, 12, or 24, the stimulation cycling protocol is typically more complex, and is typically configured to cause current to pass through or close to most or all fibers in the nerve at the longitudinal site where the ring of electrodes is placed. One such complex protocol includes effectively creating a star out of the current lines passing through the nerve, or ensuring that each electrode in the ring conveys current to some, most, or all of the other electrodes.

Advantageously, due to the very high application rate of the current from the different electrodes compared to the relatively-low biological response rate of the fibers within the nerve, the fibers at that longitudinal site are effectively all stimulated at substantially the same time. In this manner, a single wave of action potential propagation is initiated from the longitudinal site at substantially the same time, and can be subsequently manipulated at other sites on the nerve using techniques described herein or in one or more of the patent applications cited herein that are assigned to the assignee of the present patent application and are incorporated herein by reference. Further, unlike solid ring electrodes which surround the nerve and conduct a significant portion of their current outside of the nerve, directly to the anode or cathode adjacent thereto, a larger portion of the current is conveyed into the nerve itself using the stimulation protocols described herein. From the "perspective" of the nerve, which functions at rates considerably slower than the switching rate of the ring of electrodes, it is as if a large portion of its nerve fibers were simultaneously stimulated.

In some embodiments of the present invention, an electrode assembly for applying current to a nerve having a longitudinal axis comprises a ring of two or more cathodes and a ring of two or more anodes, each ring of electrodes adapted to be placed around the nerve axis, at a respective cathodic or anodal longitudinal site of the nerve. Typically, a control unit drives an anode in the ring of anodes to drive current through the nerve to a cathode typically at another orientation with respect to the axis, in order to stimulate fibers in the nerve nearer the cathode. Thus, for example, if each ring has twelve electrodes, then in one stimulation protocol, the anode at "12 o'clock" with respect to the axis drives current generally through the nerve to the cathode at 6 o'clock. After a very short delay (typically 10-100 microseconds), the anode at 1 o'clock drives current generally through the nerve to the cathode at 7 o'clock. The pattern is typically continued for all of the electrodes. It will be appreciated by one who has read the disclosure of the present patent application that a variety of stimulation protocols may be developed, and that a suitable protocol should typically be determined in accordance with the anatomy of the nerve, the types of nerve fibers therein, and the purpose of the stimulation, among other factors.

In some embodiments of the present invention, a tubular cuff for implantation around tubular tissue is shaped so as to define: (a) a longitudinal slit having a first edge and a second edge, and (b) one or more holes in a vicinity of the first edge. The cuff comprises one or more protrusions, which are coupled to the cuff in a vicinity of the second edge, and are adapted to hold the first and second edges together when the protrusions are passed through the holes.

For some applications, the tubular cuff comprises one or more filaments, such as sutures or filaments made from silicone, which are coupled to respective protrusions. For some applications, silicone sutures are an integral portion of a silicone cuff. In order to draw the protrusions through respective holes, a surgeon threads the filaments through the respective holes, and draws the filaments until the protrusions pass through the respective holes. Upon completion of the implantation, the surgeon may clip off the filaments. In embodiments of the cuff that do not comprise filaments, the surgeon typically uses standard surgical tools, such as tweezers, to draw the protrusions through the holes.

In some embodiments of the present invention, the apparatus comprises one or more end insulating elements, which extend towards tubular tissue in order to electrically isolate a portion of the tissue within the apparatus from a portion of the tissue outside the apparatus. For some applications, the apparatus additionally comprises one or more internal insulating elements positioned between the electrodes. For some applications, the apparatus comprises more than one material, for example, to provide better control of diameters, thicknesses, and/or strengths of various portions of the cuff. For example, an outer wall of the apparatus may comprise a material having a Shore D hardness of between about 40 and about 50, while the insulating elements may comprise a material having a Shore D hardness of between about 5 and about 20, e.g., about 10. Such a hardness of the insulating elements generally reduces any stress that might otherwise develop at the contact area between the tissue and the insulating elements. Such a hardness of the outer wall generally preserves the shape of the apparatus, and generally facilitates removal of fibrosis tissue that may grow around the apparatus.

The insulating elements may be somewhat removed from the tissue, or, alternatively, the insulating elements may be disposed in physical contact with the tissue after placement of the apparatus. Such physical contact typically causes current flowing through the one or more electrodes to pass through the tissue, rather than partially between the insulating elements and the tissue. For some applications, a surface of at least one of the insulating elements that is in physical contact with the tissue is configured so as to promote connective tissue growth between the tissue and the surface. For example, the surface may be rough, so as to promote the connective tissue growth. Alternatively or additionally, (a) the surface is treated with a growth factor that promotes the connective tissue growth, such as TGF-beta 1 or TGF-beta 2, (b) talc is applied to the surface in order to stimulate fibrosis, and/or (c) a material structure, such as a plastic mesh, is applied to the surface. Such connective tissue growth generally supports the insulating contact between the insulating element and the tissue.

For some applications, the end insulating elements are configured so as to define a tissue surface axial distance between longitudinal sites on the tissue at which the insulating elements are in physical contact with the tissue. The tissue surface axial distance is less than an electrode surface axial length of the electrode. Such a configuration provides a relatively small contact surface area with the tissue, while allowing for a relatively high electrode capacitance (which depends on the surface area of the electrode).

In some embodiments of the present invention, an electrode assembly is provided for applying current to a nerve having a radius and a longitudinal central axis. The electrode assembly comprises a housing, adapted to be placed in a vicinity of the nerve; first and second anodes, fixed to the housing; and a cathode, fixed to the housing between the first and second anodes. For some applications, a first distance between a longitudinal center of the first anode and a longitudinal center of the cathode, and a second distance between a longitudinal center of the second anode and a longitudinal center of the cathode are each at least 1 times (e.g., at least 1.5 times or at least 2 times) the radius of the nerve.

In some embodiments of the present invention, an electrode assembly is provided for applying current to a nerve. The electrode assembly comprises a housing, and one or more electrodes fixed to the housing. For some applications, the electrodes are fixed to the housing so as to define a closest electrode distance to the surface of the nerve that is less than about 0.5 mm. For example, one or more of the electrodes may be in direct physical contact with the nerve when the electrode assembly is applied to the nerve. The housing is shaped so as to define an outer surface having one or more holes therethrough, such that biological materials and body fluids can pass through into chambers defined by the nerve, the housing, and the electrodes. After implantation of the electrode assembly, fibrosis tissue typically grows in the chambers, thereby providing electrical insulation within the chambers.

There is therefore provided, in accordance with an embodiment of the present invention, apparatus for applying current to a nerve, including:

a cathode, adapted to be placed in a vicinity of a cathodic longitudinal site of the nerve and to apply a cathodic current to the nerve;

a primary inhibiting anode, adapted to be placed in a vicinity of a primary anodal longitudinal site of the nerve and to apply a primary anodal current to the nerve; and a secondary inhibiting anode, adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site.

In an embodiment, the apparatus is adapted to be placed on the nerve such that, relative to the anodal longitudinal sites, the cathodic longitudinal site is proximal to a brain of a subject, the subject including the nerve. Alternatively, the apparatus is adapted to be placed on the nerve such that, relative to the anodal longitudinal sites, the cathodic longitudinal site is distal to a brain of a subject, the subject including the nerve.

In an embodiment, the primary inhibiting anode is adapted to apply the primary anodal current to the nerve so as to block propagation of action potentials past the primary anodal longitudinal site.

For some applications, the primary inhibiting anode is adapted to apply the primary anodal current to the nerve so as to block propagation past the primary anodal longitudinal site of action potentials in a first set of nerve fibers, and to allow propagation past the primary anodal longitudinal site of action potentials in a second set of nerve fibers, the second set of nerve fibers having characteristic diameters generally smaller than characteristic diameters of the nerve fibers in the first set.

In an embodiment, the cathode includes a plurality of cathodes, placed in the vicinity of the cathodic longitudinal site of the nerve, at respective positions around an axis of the nerve. In this case, the plurality of cathodes are typically adapted to apply the cathodic current at a characteristic frequency greater than 1000 Hz.

Typically, the apparatus includes a primary insulating element disposed between the cathode and the primary inhibiting anode. The primary insulating element is typically disposed in a position with respect to the cathode and the primary inhibiting anode so as to guide the flow of current between the cathode and the primary inhibiting anode. For some applications, the apparatus includes a secondary insulating element, disposed between the primary inhibiting anode and the secondary inhibiting anode. In this case, a characteristic size of the secondary insulating element is typically smaller than a characteristic size of the primary insulating element. Alternatively or additionally, a characteristic distance of the secondary insulating element to an axis of the nerve is greater than a characteristic distance of the primary insulating element to the axis of the nerve.

In some embodiments, the apparatus includes a tertiary inhibiting electrode, adapted to be placed in a vicinity of a tertiary anodal longitudinal site of the nerve and to apply a tertiary anodal current to the nerve, the tertiary anodal longitudinal site being closer to the secondary anodal longitudinal site than to the primary anodal longitudinal site. In an embodiment, the tertiary inhibiting anode is configured such that a current density of the tertiary anodal current is of lower magnitude than a magnitude of a current density of the secondary anodal current.

Typically, the apparatus includes a housing, coupled to the cathode, the primary inhibiting anode and the secondary inhibiting anode, adapted to facilitate placement of the cathode and the anodes in the vicinities of their respective sites. In an embodiment, the housing is configured such that an arc, defined by an extent that the housing is adapted to surround the nerve, is between about 90 and 270 degrees. Alternatively, the housing is configured such that an arc, defined by an extent that the housing is adapted to surround the nerve, is between about 270 and 359 degrees.

Typically, a closest cathode distance to an axis of the nerve, a closest primary inhibiting anode distance to the axis, and a closest secondary inhibiting anode distance to the axis are all at least approximately 1.5 times the radius of the nerve.

For some applications, the secondary inhibiting anode is configured such that a secondary anodal current density induced by the secondary anodal current is of lower magnitude than a magnitude of a primary anodal current density induced by the primary anodal current. In an embodiment, the primary anodal current is substantially of the same magnitude as the secondary anodal current. In an embodiment, a characteristic surface area of the secondary inhibiting anode is higher than a characteristic surface area of the primary inhibiting anode. For example, the characteristic surface area of the secondary inhibiting anode may be at least 2 times the characteristic surface area of the primary inhibiting anode.

In an embodiment, the secondary inhibiting anode is configured such that a current density of the secondary anodal current is of lower magnitude than a magnitude of a current density of the primary anodal current. In this case, a characteristic surface area of the primary inhibiting anode may be higher than a characteristic surface area of the secondary inhibiting anode, and a common voltage may be applied to the primary inhibiting anode and to the secondary inhibiting anode.

For some applications:

(a) the primary inhibiting anode is adapted to have associated therewith a primary level of electrical impedance between the primary inhibiting anode and the nerve, when in the vicinity of the primary anodal longitudinal site, and (b) the secondary inhibiting anode is adapted to have associated therewith a secondary level of electrical impedance between the secondary inhibiting anode and the nerve when in the vicinity of the secondary anodal longitudinal site, the secondary level of impedance having a higher magnitude than the primary level of impedance.

In an embodiment, the secondary inhibiting anode is adapted to be coupled to the housing so as to define a secondary anode distance to an axis of the nerve, and wherein the primary inhibiting anode is adapted to be coupled to the housing so as to define a primary anode distance to the axis of the nerve that is smaller than the secondary anode distance. For example, a ratio of the secondary anode distance to the primary anode distance may be greater than approximately 1.5:1.

In an embodiment, the apparatus includes a primary fiber-selection anode, adapted to be placed in a vicinity of a primary fiber-selection anodal longitudinal site of the nerve that is closer to the cathodic longitudinal site than to the primary anodal longitudinal site. For example, the apparatus may include a secondary fiber-selection anode, adapted to be placed in a vicinity of a secondary fiber-selection anodal longitudinal site of the nerve that is closer to the primary fiber-selection anodal longitudinal site than to the cathodic longitudinal site.

Typically, the apparatus includes a control unit, adapted to drive the cathode to apply the cathodic current to the nerve, adapted to drive the primary inhibiting anode to apply the primary anodal current to the nerve, and adapted to drive the secondary inhibiting anode to apply the secondary anodal current to the nerve. In one embodiment, the apparatus includes a first resistive element coupled between the control unit and the primary inhibiting anode, and a second resistive element coupled between the control unit and the secondary inhibiting anode, the second resistive element having a resistance higher than a resistance of the first resistive element.

For some applications, the apparatus includes exactly one lead that leaves the control unit for coupling the control unit to the primary and secondary inhibiting anodes. Alternatively, the apparatus includes respective leads that leave the control unit and couple the control unit to the primary and secondary inhibiting anodes.

The control unit is typically adapted to configure a current density of the secondary anodal current to be of lower magnitude than a current density of the primary anodal current. In an embodiment, the control unit is adapted to configure an amplitude of a current density of the cathodic current to be between 1.1 and 2 times greater than an amplitude of a current density of the primary anodal current. Alternatively or additionally, the control unit is adapted to configure an amplitude of a current density of the cathodic current to be between 3 and 6 times greater than an amplitude of a current density of the secondary anodal current. Further alternatively or additionally, the control unit is adapted to configure an amplitude of a current density of the primary anodal current to be at least 2 times greater than an amplitude of a current density of the secondary anodal current.

There is also provided, in accordance with an embodiment of the present invention, apparatus for applying current to a nerve having a radius and a longitudinal central axis, including:

a housing, adapted to be placed in a vicinity of the nerve; and a cathode and an anode, fixed to the housing so as to define, when the housing is placed in the vicinity of the nerve, respective closest cathode and anode distances to the axis that are both at least approximately 1.5 times greater than the radius of the nerve.

Typically, the closest cathode and anode distances to the axis are both at least approximately 2 times greater than the radius of the nerve.

In an embodiment, the cathode includes a plurality of cathodes, placed in the vicinity of the cathodic longitudinal site of the nerve, at respective positions around the axis of the nerve, each of the respective positions being at a distance from the axis at least 1.5 times greater than the radius of the nerve.

In an embodiment, the apparatus includes an insulating element disposed between the cathode and the anode. A characteristic distance of the insulating element to the axis of the nerve is typically at least 1.5 times greater than the radius of the nerve. For some applications, the distance of the anode to the axis is substantially the same as a characteristic distance of the insulating element to the axis of the nerve. For other applications, the distance of the anode to the axis is greater than a characteristic distance of the insulating element to the axis of the nerve. For example, the distance of the anode to the axis may be within 30% of the characteristic distance of the insulating element to the axis of the nerve plus a width of the anode.

There is further provided, in accordance with an embodiment of the present invention, apparatus for applying current to a nerve having a radius and a longitudinal central axis, including:

a housing, adapted to be placed in a vicinity of the nerve;

first and second electrodes, fixed to the housing; and an insulating element, fixed to the housing between the first and second electrodes so as to define a characteristic closest insulating element distance to the central axis that is at least approximately 1.5 times greater than the radius of the nerve.

In an embodiment, the insulating element is adapted to be placed in the vicinity of the nerve at a longitudinal site that is between respective longitudinal sites of the first and second electrodes. Alternatively, the insulating element is adapted to be placed in the vicinity of the nerve at a site with respect to the axis of the nerve that is between respective sites of the first and second electrodes, with respect to the axis.

There is still further provided, in accordance with an embodiment of the present invention, apparatus for applying current to a nerve, including:

a cathode, adapted to be placed in a vicinity of a cathodic site of the nerve; and a plurality of anodes, adapted to be placed in a vicinity of respective anodal longitudinal sites of the nerve and to apply respective anodal currents to the nerve, that define, in combination, an anodal activation function having: (a) a hyperpolarizing portion thereof having a maximum hyperpolarizing amplitude, and (b) a depolarizing portion thereof, having a maximum depolarizing amplitude corresponding to a depolarizing site on the nerve distal with respect to the cathode to a site corresponding to the hyperpolarizing portion, wherein the maximum hyperpolarizing amplitude is at least five times greater than the maximum depolarizing amplitude.

In an embodiment, the apparatus includes a housing to which the cathode and the plurality of anodes are coupled, wherein a distance of a first one of the anodes to an axis of the nerve is less than a distance of a second one of the anodes to the axis, the first one of the anodes being coupled to the housing closer to the cathode than the second one of the anodes.

Alternatively or additionally, the apparatus includes a housing to which the cathode and the plurality of anodes are coupled, wherein a surface area of a first one of the anodes is less than a surface area of a second one of the anodes, the first one of the anodes being coupled to the housing closer to the cathode than the second one of the anodes.

Typically, the apparatus includes a housing to which the cathode and the plurality of anodes are coupled, and one of the anodes is positioned within the housing so as to reduce a virtual cathode effect induced by another one of the anodes.

The cathode and anodes are typically disposed such that a first one of the anodal longitudinal sites is between the cathodic site and a second one of the anodal longitudinal sites. In an embodiment, the anodes are disposed such that the second one of the anodal longitudinal sites is between the first one of the anodal longitudinal sites and a third one of the anodal longitudinal sites. Typically, the anodes are adapted such that a current density of the anodal current applied at the second one of the anodal longitudinal sites has a lower magnitude than a magnitude of a current density of the anodal current applied at the first one of the anodal longitudinal sites.

For some applications, the anodes are adapted such that a ratio of the current density of the anodal current applied at the first site to the current density of the anodal current applied at the second site is at least 2:1. Typically, the anodes are adapted such that a ratio of the current density of the anodal current applied at the first site to the current density of the anodal current applied at the second site is at least 5:1.

There is yet further provided, in accordance with an embodiment of the present invention, apparatus for applying current to a nerve, including:

a cathode, adapted to be placed in a vicinity of a first longitudinal site of the nerve; and an elongated anode, adapted to be placed in a vicinity of a second longitudinal site of the nerve, and, when so placed, to have associated therewith: (a) a first level of electrical impedance between the nerve and a location on the elongated anode proximal to the cathode, and (b) a second level of electrical impedance, greater than the first level, between the nerve and a location on the elongated anode distal to the cathode.

Typically, the apparatus includes a coating disposed on a surface of the elongated anode, configured to provide the first and second levels of impedance. In an embodiment, the coating is disposed on the surface in different respective thicknesses at the two locations on the elongated anode. Alternatively or additionally, the coating includes a coating that has undergone a surface treatment, and wherein the coating is configured to provide the first and second levels of impedance responsive to having undergone the surface treatment. In an embodiment, the coating includes iridium oxide, titanium nitrite, and/or platinum iridium.

There is also provided, in accordance with an embodiment of the present invention, apparatus for applying current to a nerve having a longitudinal axis, including:

two or more electrodes, adapted to be placed in a vicinity of a longitudinal site of the nerve, at respective positions around the axis; and a control unit, adapted to:

(a) drive current between two of the electrodes, thereby defining a first pair of the electrodes and a first direction of current flow, and, less than one millisecond later, (b) drive current between two of the electrodes, thereby defining a second pair of the electrodes and a second direction of current flow, and (c) cycle between steps (a) and (b) at a rate greater than 1000 Hz, wherein at least either the first pair of electrodes is different from the second pair of electrodes or the first direction of current flow is different from the second direction of current flow.

Typically, the two or more electrodes include three or more electrodes, or four or more electrodes.

For some applications, the control unit is adapted to set the rate to be greater than 4000 Hz.

There is yet additionally provided, in accordance with an embodiment of the present invention, apparatus for applying current to a nerve having a longitudinal axis, including:

a set of two or more cathodes, adapted to be placed in a vicinity of a cathodic longitudinal site of the nerve, at respective positions around the axis; and a set of two or more anodes, adapted to be placed in a vicinity of an anodal longitudinal site of the nerve, at respective positions around the axis.

As appropriate, the two or more cathodes may include six or more cathodes, e.g., twelve or more cathodes.

The apparatus typically includes a control unit, adapted to drive current between respective ones of the cathodes and respective ones of the anodes. The control unit is typically adapted to cycle the current driving at a rate greater than 1000 Hz. In an embodiment, the control unit is adapted to complete a sweep of driving the current through substantially all of the cathodes in less than 1000 microseconds. Typically, the control unit is adapted to complete a sweep of driving the current through substantially all of the cathodes in less than 100 microseconds.

There is still additionally provided, in accordance with an embodiment of the present invention, a method for applying current to a nerve, including:

applying cathodic current in a vicinity of a cathodic longitudinal site of the nerve;

applying a primary anodal current to the nerve in a vicinity of a primary anodal longitudinal site of the nerve; and applying a secondary anodal current to the nerve in a vicinity of a secondary anodal longitudinal site of the nerve that is closer to the primary anodal longitudinal site than to the cathodic longitudinal site.

There is yet additionally provided, in accordance with an embodiment of the present invention, a method for applying current to a nerve having a radius and a longitudinal central axis, including applying cathodic and anodal current to the nerve from respective cathodic and anodal current-application sites that are both located at distances from the axis of the nerve which are at least approximately 1.5 times greater than the radius of the nerve.

There is also provided, in accordance with an embodiment of the present invention, a method for applying current to a nerve, including:

applying cathodic current in a vicinity of a cathodic site of the nerve; and applying anodal currents in a vicinity of respective anodal longitudinal sites of the nerve, the currents defining, in combination, an anodal activation function having: (a) a hyperpolarizing portion thereof having a maximum hyperpolarizing amplitude, and (b) a depolarizing portion thereof, having a maximum depolarizing amplitude corresponding to a depolarizing site on the nerve distal, with respect to the cathodic site, to a site corresponding to the hyperpolarizing portion, wherein the maximum hyperpolarizing amplitude is at least five times greater than the maximum depolarizing amplitude.

There is further provided, in accordance with an embodiment of the present invention, a method for applying current to a nerve having a longitudinal axis, including driving current between: (a) a set of two or more cathodic sites in a vicinity of a first longitudinal site of the nerve, which are located at respective positions around the axis, and (b) a set of two or more anodal sites in a vicinity of a second longitudinal site of the nerve, which are located at respective positions around the axis.

There is still further provided, in accordance with an embodiment of the present invention, apparatus including an implantable tubular cuff, the cuff:

shaped so as to define: (a) a longitudinal slit having a first edge and a second edge, and (b) at least one hole in a vicinity of the first edge; and including at least one protrusion, which is coupled to the cuff in a vicinity of the second edge, and is adapted to hold the first and second edges together when the protrusion is passed through the hole and when the cuff is disposed within a body of a subject and surrounding longitudinal tissue of the subject.

For some applications, the cuff is shaped so as to define a plurality of holes in the vicinity of the first edge, and the cuff includes a plurality of protrusions, which are coupled to the cuff in the vicinity of the second edge, and are adapted to hold the first and second edges together when each of the protrusions is passed through a respective one of the holes.

In an embodiment, the cuff includes at least one electrode. For some applications, the cuff includes two electrodes and an insulating element disposed therebetween.

In an embodiment, the cuff includes a first flexible resilient material, and the insulating element includes a second flexible resilient material, the first material having a hardness different from a hardness of the second material.

In an embodiment, the cuff includes a tab coupled to the first edge, the tab configured to aid in drawing the protrusion through the hole when the tab is moved toward the protrusion.

For some applications, the cuff includes at least one flexible resilient material having a Shore D hardness between about 4 and about 80.

In an embodiment, the cuff includes a first flexible resilient material in a vicinity of the hole, and a second flexible resilient material, the first material having a hardness different from a hardness of the second material. In an embodiment, the cuff includes a first flexible resilient material in a vicinity of the protrusion, and a second flexible resilient material, the first material having a hardness different from a hardness of the second material.

In an embodiment, the cuff includes a filament coupled to the protrusion. For some applications, the filament is formed as an integral portion of the cuff. For some applications, the cuff is configured so that when the filament is drawn through the hole, the protrusion is drawn through the hole thereafter.

In an embodiment, the tissue includes a nerve of the subject, and the cuff is adapted to be placed around the nerve. Alternatively, the tissue includes a blood vessel of the subject, and the cuff is adapted to be placed around the blood vessel. Further alternatively, the tissue is selected from the list consisting of: a muscle of the subject, a tendon of the subject, a ligament of the subject, an esophagus of the subject, intestine of the subject, and a fallopian tube of the subject, and the cuff is adapted to be placed around the selected tissue.

In an embodiment, the first edge includes a flap, adapted to come in contact with a portion of the cuff in the vicinity of the second edge when the first and second edges are held together. For some applications, when no external force is applied to the cuff, the flap forms an angle of between about 90 and about 180 degrees with a surface of the cuff in the vicinity of the first edge. For some applications, the flap includes a tab, configured to help draw the protrusion through the hole when the tab is moved toward the protrusion.

In an embodiment, each of the protrusions includes a head portion and a neck portion, the head portion having a perimeter greater than a perimeter of the neck portion. For some applications, a perimeter of the head portion is greater than a perimeter of the hole.

For some applications, the protrusion is adapted to be passed through the hole such that the head portion passes through the hole, and the neck portion remains substantially in the hole. For some applications, the head portion has an initial shape prior to being passed through the hole, and is adapted to (a) assume a different shape while being passed through the hole, and (b) substantially return to the initial shape thereof after being passed through the hole.

For some applications, the head portion includes a first flexible resilient material having a first hardness, and a portion of the cuff excluding the head portion includes a second flexible resilient material having a second hardness, the first hardness different from the second hardness. For some applications, the cuff includes a filament coupled to the neck portion.

In an embodiment, the cuff is configured so that when the filament is drawn through the hole, the head portion is drawn through the hole thereafter.

There is additionally provided, in accordance with an embodiment of the present invention, a method for enclosing a section of longitudinal tissue of a subject with a tubular cuff, the method including:

separating a first edge of a longitudinal slit defined by the cuff from a second edge of the slit;

placing the cuff within a body of the subject around the section of the tissue; and passing at least one protrusion coupled to the cuff in a vicinity of the first edge, through at least one hole defined by the cuff in a vicinity of the second edge, so as to hold the first and second edges together.

There is yet additionally provided, in accordance with an embodiment of the present invention, a method for stimulating a vagus nerve of a subject, including:

applying to the vagus nerve a first electrode device, the first electrode device having a first characteristic diameter;

driving the electrodes of the first electrode device to apply a current to the vagus nerve;

measuring a reduction in heart rate of the subject responsive to driving the electrodes of the first electrode device to apply the current;

determining whether the reduction in heart rate is less than about 10%; and responsive to determining that the reduction in heart rate is less than about 10%, removing the first electrode device from the nerve and applying to the vagus nerve a second electrode device, the second electrode device having a second characteristic diameter smaller than the first characteristic diameter.

For some applications, applying the first electrode device includes:

applying the first electrode device, wherein the first characteristic diameter corresponds to a characteristic distance of electrodes of the first electrode device from an axis of the nerve when the first electrode device is applied to the nerve, and wherein the second characteristic diameter corresponds to a characteristic distance of electrodes of the second electrode device from an axis of the nerve when the second electrode device is applied to the nerve, the second characteristic distance being smaller than the first characteristic distance.

Alternatively or additionally, applying the first electrode device includes:

applying the first electrode device, wherein the first characteristic diameter corresponds to a characteristic distance of an insulating element of the first electrode device from an axis of the nerve when the first electrode device is applied to the nerve, and wherein the second characteristic diameter corresponds to a characteristic distance of an insulating element of the second electrode device from an axis of the nerve when the second electrode device is applied to the nerve, the second characteristic distance being smaller than the first characteristic distance.

There is also provided, in accordance with an embodiment of the present invention, apparatus for applying current to a nerve having a radius and a longitudinal central axis, the apparatus including:

a housing, adapted to be placed in a vicinity of the nerve;

first and second anodes, fixed to the housing;

a cathode, fixed to the housing between the first and the second anodes so as to define a first distance between a longitudinal center of the first anode and a longitudinal center of the cathode, and a second distance between a longitudinal center of the second anode and the longitudinal center of the cathode, the first and the second distances each at least 1, 1.5, or 2 times a closest cathodic distance to the central axis of the nerve when the housing is placed in the vicinity of the nerve; and a control unit, adapted to drive the cathode and the first and second anodes to apply a current to the nerve, the control unit adapted to:

drive first intervening electrodes, if any, fixed to the housing between the first anode and the cathode to apply less than 20% of the current applied by the cathode, e.g., less than 10% or less than 5%, and drive second intervening electrodes, if any, fixed to the housing between the second anode and the cathode to apply less than 20% of the current applied by the cathode, e.g., less than 10% or less than 5%.

There is further provided, in accordance with an embodiment of the present invention, apparatus for applying current to a nerve having a radius and a longitudinal central axis, including:

a housing, adapted to be placed in a vicinity of the nerve;

first and second anodes, fixed to the housing;

a cathode, fixed to the housing between the first and the second anodes so as to define a first distance between a longitudinal center of the first anode and a longitudinal center of the cathode, and a second distance between a longitudinal center of the second anode and the longitudinal center of the cathode; and a control unit, adapted to drive the cathode and anodes to apply a current to the nerve that:

hyperpolarizes longitudinal anodal regions in respective vicinities of the anodes, generates at least one depolarization peak in a vicinity of the cathode, and hyperpolarizes longitudinal cathodic regions surrounding the at least one depolarization peak, each of the cathodic regions having an overlapping portion that overlaps a respective anodal region, the first and the second distances each sufficiently large such that a maximum cathodically-hyperpolarized amplitude of each of the overlapping portions is less than 0.2 times, e.g., less than 0.1 times or less than 0.05 times, a depolarized amplitude of the at least one depolarization peak.

There is still further provided, in accordance with an embodiment of the present invention, apparatus for applying current to a nerve having a radius and a longitudinal central axis, the apparatus including:

a housing, adapted to be placed in a vicinity of the nerve;

first and second anodes, fixed to the housing; and a cathode, fixed to the housing between the first and the second anodes so as to define a first distance between a longitudinal center of the first anode and a longitudinal center of the cathode, and a second distance between a longitudinal center of the second anode and the longitudinal center of the cathode, the first and the second distances each at least 1, 1.5, or 2 times a closest cathodic distance to the central axis of the nerve when the housing is placed in the vicinity of the nerve, the cathode and the first and second anodes fixed to the housing such that a closest electrode distance is less than 3 times, e.g., less than 2 or less than 1 times, the radius of the nerve, the closest electrode distance selected from the list consisting of: the closest cathodic distance, a closest first anode distance to the central axis of the nerve, and a closest second anode distance to the central axis of the nerve.

There is also provided, in accordance with an embodiment of the present invention, apparatus for applying current to a nerve, including:

a housing, configured to be placed in a vicinity of the nerve;

at least one electrode, fixed to the housing such that the at least one electrode does not come in direct physical contact with the nerve when the housing is placed in the vicinity of the nerve, and such that the electrode surrounds greater than 180 degrees of a circumference of the nerve after the placement of the housing; and two end insulating elements, fixed to the housing such that the at least one electrode is between the end insulating elements, and the end insulating elements come in contact or practically in contact with the nerve when the housing is placed in the vicinity of the nerve.

Typically, the end insulating elements are fixed to the housing so as to define a characteristic closest end insulating element distance to a surface of the nerve that is less than 0.5 mm, when the housing is placed in the vicinity of the nerve.

For some applications, at least one of the end insulating elements is shaped so as to define a rough surface that is in physical contact with the nerve when the housing is placed in the vicinity of the nerve.

For some applications, the at least one electrode is fixed to the housing so as to define a closest electrode distance to a longitudinal central axis of the nerve that is at least 1 mm. Alternatively, the at least one electrode is fixed to the housing so as to define a closest electrode distance to the surface of the nerve that is at least 0.5 mm.

For some applications, the at least one electrode is fixed to the housing so as to define a closest electrode distance to a longitudinal central axis of the nerve that is at least 1.1 times a radius of the nerve. Alternatively, the at least one electrode is fixed to the housing so as to define a closest electrode distance to a longitudinal central axis of the nerve that is at least 1.5 times a radius of the nerve. Further alternatively, the at least one electrode is fixed to the housing so as to define a closest electrode distance to a longitudinal central axis of the nerve that is at least 2 times a radius of the nerve.

For some applications, the housing includes an outer insulating wall not in physical contact with the nerve when the housing is in the vicinity of the nerve, the wall having a Shore D hardness of at least 40.

For some applications, the at least one electrode includes exactly one set of one or more electrodes having respective electrode surfaces that are in electrical contact with the nerve and are in electrical contact with each other via a path outside of the nerve.

For some applications, the housing and the end insulating elements are an integrated unit.

For some applications, the housing is shaped so as to define an external surface, configured to promote growth of fibrous connective tissue therearound.

For some applications, the end insulating elements are shaped so as to define, upon placement of the housing in the vicinity of the nerve, a nerve axial distance between the end insulating elements that is less than an electrode surface axial length of the at least one electrode. For some applications, the electrode surface axial length is between 1.5 and 5 times the nerve axial distance.

For some applications, at least one of the end insulating elements is shaped so as to define a contact surface between the end insulating element and the nerve, and the contact surface is configured so as to promote connective tissue growth between the nerve and the contact surface. For some applications, the contact surface is configured so as to promote the connective tissue growth in such a manner so as to provide insulation between the nerve and the contact surface. For some applications, the contact surface is treated with a growth factor that can promote the connective tissue growth. For some applications, the contact surface includes a mesh that is adapted to promote the connective tissue growth.

In an embodiment, the end insulating elements are fixed to the housing so as to be in physical contact with the nerve after placement of the housing. For some applications, the end insulating elements are fixed to the housing so as to be in physical contact with the nerve immediately upon the placement of the housing. Alternatively, the end insulating elements are fixed to the housing so as to be in physical contact with the nerve after a period of adaptation of the nerve to the placement of the housing. For some applications, the end insulating elements are fixed to the housing so as to be in direct physical contact with the nerve. Alternatively, the end insulating elements are adapted to be in indirect physical contact with the nerve via connective tissue that grows after the placement of the housing.

In an embodiment, the at least one electrode includes at least a first electrode and a second electrode, and the apparatus includes an internal insulating element fixed to the housing between the first and second electrodes, so as to define a closest internal insulating element distance to the surface of the nerve that is less than 0.5 mm. For some applications, the internal insulating element is fixed to the housing so as to be in physical contact with the nerve after placement of the housing.

In an embodiment, the at least one electrode includes at least first, second, and third electrodes, and the apparatus includes first and second internal insulating elements fixed to the housing between the first and the second electrodes, and between the second and the third electrodes, respectively, so as to define closest internal insulating element distances to the surface of the nerve that are each less than 0.5 mm. For some applications, the internal insulating elements are fixed to the housing so as to be in physical contact with the nerve after placement of the housing. For some applications, the first and second internal insulating elements are shaped to define, upon placement of the housing, a nerve axial distance between the first and second internal insulating elements that is less than an electrode surface axial length of the second electrode. For some applications, the electrode surface axial length is between 1.5 and 5 times the nerve axial distance.

For some applications, the at least one electrode includes one or more materials selected from the list consisting of: platinum, a platinum alloy, titanium, and a titanium alloy. For some applications, the at least one electrode includes substantially only the one or more materials. For some applications, the apparatus includes at least one lead coupled to the at least one electrode, the at least one lead including:

a first portion thereof within 2 cm of a surface of the at least one electrode closest to the nerve, the first portion including substantially only the one or more materials; and a second portion thereof greater than 2 cm from the surface of the at least one electrode closest to the nerve, the second portion including a conductive material.

For some applications, the housing includes an outer insulating wall not in physical contact with the nerve when the housing is in the vicinity of the nerve, and at least a portion of the outer insulating wall has a hardness greater than a hardness of at least a portion of at least one of the end insulating elements. For some applications, the at least a portion of the outer insulating wall has a Shore D hardness of between 40 and 50, and the at least a portion of the at least one of the end insulating elements has a Shore D hardness of between 5 and 20. For example, the at least a portion of the end insulating elements may have a Shore D hardness of 10.

For some applications, the at least one electrode is adapted to substantially completely surround the nerve after the placement of the housing. For some applications, the housing includes an outer insulating wall not in physical contact with the nerve when the housing is in the vicinity of the nerve, and at least a portion of the outer insulating wall has a hardness greater than a hardness of at least a portion of at least one of the end insulating elements. For some applications, the at least a portion of the outer insulating wall has a Shore D hardness of between 40 and 50, and the at least a portion of the at least one of the end insulating elements has a Shore D hardness of between 5 and 20. For example, the at least a portion of the at least one of the end insulating elements may have a Shore D hardness of 10.

There is further provided, in accordance with an embodiment of the present invention, apparatus for applying current to a nerve, including:

a housing, adapted to be placed in a vicinity of the nerve;

at least one electrode, fixed to the housing, such that the at least one electrode does not come in direct physical contact with the nerve, and such that the electrode surrounds more than 180 degrees of a circumference of the nerve; and two end insulating elements, fixed to the housing such that the at least one electrode is between the end insulating elements, the end insulating elements adapted to be in physical contact with the nerve after placement of the housing.

For some applications, the end insulating elements are adapted to be in physical contact with the nerve immediately upon the placement of the housing. Alternatively, the end insulating elements are adapted to be in physical contact with the nerve after a period of adaptation of the nerve to the placement of the housing.

For some applications, the end insulating elements are adapted to be in direct physical contact with the nerve. Alternatively, the end insulating elements are adapted to be in indirect physical contact with the nerve via connective tissue that grows after the placement of the housing.

There is still further provided, in accordance with an embodiment of the present invention, apparatus for applying current to a nerve, including:

a housing, configured to be placed in a vicinity of the nerve;

first and second electrodes, fixed to the housing at respective first and second longitudinal sites of the housing, such that the first and second electrodes do not come in direct physical contact with the nerve when the housing is placed in the vicinity of the nerve;

an internal insulating element, fixed to the housing between the first and second longitudinal sites; and two end insulating elements, fixed to the housing such that the first and second longitudinal sites are between the end insulating elements, and the end insulting elements come in contact or practically in contact with the nerve when the housing is placed in the vicinity of the nerve.

Typically, the end insulating elements are fixed to the housing so as to define a characteristic closest end insulating element distance to a surface of the nerve that is less than 0.5 mm, when the housing is placed in the vicinity of the nerve.

For some applications, at least one of the end insulating elements is shaped so as to define a rough surface that is in physical contact with the nerve when the housing is placed in the vicinity of the nerve.

For some applications, the first and second electrodes are fixed to the housing so as to define a closest electrode distance to a longitudinal central axis of the nerve that is at least 1 mm. Alternatively, the first and second electrodes are fixed to the housing so as to define a closest electrode distance to the surface of the nerve that is at least 0.5 mm.

For some applications, the first and second electrodes are fixed to the housing so as to define a closest electrode distance to a longitudinal central axis of the nerve that is at least 1.1 times a radius of the nerve. For some applications, the first and second electrodes are fixed to the housing so as to define a closest electrode distance to a longitudinal central axis of the nerve that is at least 1.5 times a radius of the nerve. For some applications, the first and second electrodes are fixed to the housing so as to define a closest electrode distance to a longitudinal central axis of the nerve that is at least 2 times a radius of the nerve.

For some applications, the housing includes an outer insulating wall not in physical contact with the nerve when the housing is placed in the vicinity of the nerve, the wall having a Shore D hardness of at least 40.

For some applications, the housing and the end insulating elements are an integrated unit.

For some applications, the housing is shaped so as to define an external surface, configured to promote growth of fibrous connective tissue therearound.

For some applications, the first and second electrodes are configured to surround greater than 180 degrees of a circumference of the nerve after the placement of the housing. For some applications, the first and second electrodes are adapted to substantially completely surround the nerve after the placement of the housing.

For some applications, the end insulating elements are shaped so as to define, upon placement of the housing in the vicinity of the nerve, a nerve axial distance between the end insulating elements that is less than an electrode surface axial length of the at least one electrode. For some applications, the electrode surface axial length is between 1.5 and 5 times the nerve axial distance.

For some applications, at least one of the end insulating elements is shaped so as to define a contact surface between the end insulating element and the nerve, and the contact surface is configured so as to promote connective tissue growth between the nerve and the contact surface. For some applications, the contact surface is configured so as to promote the connective tissue growth in such a manner so as to provide insulation between the nerve and the contact surface. For some applications, the contact surface is treated with a growth factor that can promote the connective tissue growth. For some applications, the contact surface includes a mesh that is adapted to promote the connective tissue growth.

For some applications, the end insulating elements are fixed to the housing so as to be in physical contact with the nerve after placement of the housing. For some applications, the end insulating elements are fixed to the housing so as to be in physical contact with the nerve immediately upon the placement of the housing. For some applications, the end insulating elements are fixed to the housing so as to be in physical contact with the nerve after a period of adaptation of the nerve to the placement of the housing. For some applications, the end insulating elements are fixed to the housing so as to be in direct physical contact with the nerve. Alternatively, the end insulating elements are adapted to be in indirect physical contact with the nerve via connective tissue that grows after the placement of the housing.

For some applications, the internal insulating element is fixed to the housing so as to define a closest internal insulating element distance to the surface of the nerve that is less than 0.5 mm. For some applications, the internal insulating element is fixed to the housing so as to be in physical contact with the nerve after placement of the housing.

For some applications, the housing includes an outer insulating wall not in physical contact with the nerve when the housing is in the vicinity of the nerve, and at least a portion of the outer insulating wall has a hardness greater than a hardness of at least a portion of at least one of the end insulating elements. For some applications, the at least a portion of the outer insulating wall has a Shore D hardness of between 40 and 50, and the at least a portion of the at least one of the end insulating elements has a Shore D hardness of between 5 and 20. For example, the at least a portion of the end insulating elements may have a Shore D hardness of 10.

There is yet further provided, in accordance with an embodiment of the present invention, apparatus for applying current to a nerve, including:

a housing, adapted to be placed in a vicinity of the nerve;

first and second electrodes, fixed to the housing at respective first and second longitudinal sites of the housing, such that the first and second electrodes do not come in direct physical contact with the nerve;

an internal insulating element, fixed to the housing between the first and second longitudinal sites; and two end insulating elements, fixed to the housing such that the first and second longitudinal sites are between the end insulating elements, the end insulating elements adapted to be in physical contact with the nerve after placement of the housing.

For some applications, the end insulating elements are adapted to be in physical contact with the nerve immediately upon the placement of the housing. Alternatively, the end insulating elements are adapted to be in physical contact with the nerve after a period of adaptation of the nerve to the placement of the housing.

For some applications, the end insulating elements are adapted to be in direct physical contact with the nerve. Alternatively, the end insulating elements are adapted to be in indirect physical contact with the nerve via connective tissue that grows after the placement of the housing.

There is also provided, in accordance with an embodiment of the present invention, apparatus for applying current to a nerve, including:

a housing, adapted to be placed in a vicinity of the nerve;

exactly one set of one or more electrodes fixed to the housing, such that the electrodes do not come in direct physical contact with the nerve, the electrodes having respective electrode surfaces that are in electrical contact with the nerve when the housing is placed in the vicinity of the nerve, and are in electrical contact with each other via a path outside of the nerve; and two end insulating elements, fixed to the housing such that the set of electrodes are between the end insulating elements, and the end insulating elements come in contact or practically in contact with the nerve when the housing is placed in the vicinity of the nerve.

Typically, the end insulating elements are fixed to the housing so as to define a characteristic closest end insulating element distance to a surface of the nerve that is less than 0.5 mm, when the housing is placed in the vicinity of the nerve.

For some applications, at least one of the end insulating elements is shaped so as to define a rough surface that is in physical contact with the nerve when the housing is placed in the vicinity of the nerve.

For some applications, the electrodes are fixed to the housing so as to define a closest electrode distance to a longitudinal central axis of the nerve that is at least 1 mm. For some applications, the electrodes are fixed to the housing so as to define a closest electrode distance to the surface of the nerve that is at least 0.5 mm.

For some applications, the electrodes are fixed to the housing so as to define a closest electrode distance to a longitudinal central axis of the nerve that is at least 1.1 times a radius of the nerve. For some applications, the electrodes are fixed to the housing so as to define a closest electrode distance to a longitudinal central axis of the nerve that is at least 1.5 times a radius of the nerve. For some applications, the electrodes are fixed to the housing so as to define a closest electrode distance to a longitudinal central axis of the nerve that is at least 2 times a radius of the nerve.

For some applications, the housing includes an outer insulating wall not in physical contact with the nerve when the housing is placed in the vicinity of the nerve, the wall having a Shore D hardness of at least 40.

For some applications, the housing is shaped so as to define an external surface, configured to promote growth of fibrous connective tissue therearound.

For some applications, at least one of the electrodes is configured to surround greater than 180 degrees of a circumference of the nerve after the placement of the housing. For some applications, the at least one of the electrodes is adapted to substantially completely surround the nerve after the placement of the housing.

For some applications, the end insulating elements are shaped so as to define, upon placement of the housing in the vicinity of the nerve, a nerve axial distance between the end insulating elements that is less than an electrode surface axial length of at least one of the electrodes. For some applications, the electrode surface axial length is between 1.5 and 5 times the nerve axial distance.

For some applications, at least one of the end insulating elements is shaped so as to define a contact surface between the end insulating element and the nerve, and the contact surface is configured so as to promote connective tissue growth between the nerve and the contact surface. For some applications, the contact surface is configured so as to promote the connective tissue growth in such a manner so as to provide insulation between the nerve and the contact surface. For some applications, the contact surface is treated with a growth factor that can promote the connective tissue growth. For some applications, the contact surface includes a mesh that is adapted to promote the connective tissue growth.

For some applications, the end insulating elements are fixed to the housing so as to be in physical contact with the nerve after placement of the housing. For some applications, the end insulating elements are fixed to the housing so as to be in physical contact with the nerve immediately upon the placement of the housing. For some applications, the end insulating elements are fixed to the housing so as to be in physical contact with the nerve after a period of adaptation of the nerve to the placement of the housing. For some applications, the end insulating elements are fixed to the housing so as to be in direct physical contact with the nerve. For some applications, the end insulating elements are adapted to be in indirect physical contact with the nerve via connective tissue that grows after the placement of the housing.

For some applications, the housing includes an outer insulating wall not in physical contact with the nerve when the housing is in the vicinity of the nerve, and at least a portion of the outer insulating wall has a hardness greater than a hardness of at least a portion of at least one of the end insulating elements. For some applications, the at least a portion of the outer insulating wall has a Shore D hardness of between 40 and 50, and the at least a portion of the at least one of the end insulating elements has a Shore D hardness of between 5 and 20. For example, the at least a portion of the end insulating elements may have a Shore D hardness of 10.

There is yet additionally provided, in accordance with an embodiment of the present invention, apparatus for applying current to a nerve, including:

a housing, adapted to be placed in a vicinity of the nerve;

exactly one set of one or more electrodes fixed to the housing, such that the electrodes do not come in direct physical contact with the nerve, the electrodes having respective electrode surfaces that are in electrical contact with the nerve and are in electrical contact with each other via a path outside of the nerve; and two end insulating elements, fixed to the housing such that the set of electrodes are between the end insulating elements, the end insulating elements adapted to be in physical contact with the nerve after placement of the housing.

For some applications, the end insulating elements are adapted to be in physical contact with the nerve immediately upon the placement of the housing. Alternatively, the end insulating elements are adapted to be in physical contact with the nerve after a period of adaptation of the nerve to the placement of the housing.

For some applications, the end insulating elements are adapted to be in direct physical contact with the nerve. Alternatively, the end insulating elements are adapted to be in indirect physical contact with the nerve via connective tissue that grows after the placement of the housing.

There is still additionally provided, in accordance with an embodiment of the present invention, apparatus for applying current to a nerve, including:

a housing, adapted to be placed in a vicinity of the nerve;

first, second, and third electrodes, fixed to the housing at first, second, and third longitudinal sites of the housing, respectively, such that the first, second, and third electrodes do not come in direct physical contact with the nerve, the second site being between the first and third sites, the second electrode having an electrode surface axial length; and first and second internal insulating elements, fixed to the housing between the first and second longitudinal sites, and between the second and third longitudinal sites, respectively, the first and second internal insulating elements shaped so as to define, upon placement of the housing, a nerve axial distance between the first and second internal insulating elements that is less than the electrode surface axial length.

For some applications, the electrode surface axial length is between 1.5 and 5 times the nerve axial distance.

For some applications, the first and second internal insulating elements are fixed to the housing so as to define a characteristic closest internal insulating element distance to a surface of the nerve that is less than 0.5 mm. For some applications, the first and second internal insulating elements are adapted to be in physical contact with the nerve after placement of the housing.

For some applications, the housing includes an outer insulating wall not in physical contact with the nerve when the housing is in the vicinity of the nerve, and at least a portion of the outer insulating wall has a hardness greater than a hardness of at least a portion of the first and second internal insulating elements. For some applications, the at least a portion of the outer insulating wall has a Shore D hardness of between 40 and 50, and the at least a portion of the first and second internal insulating elements has a Shore D hardness of between 5 and 20. For example, the at least a portion of the first and second internal insulating elements may have a Shore D hardness of 10.

There is yet additionally provided, in accordance with an embodiment of the present invention, apparatus for applying current to a nerve, including:

a housing, adapted to be placed in a vicinity of the nerve;

at least one electrode, fixed to the housing such that the at least one electrode does not come in direct physical contact with the nerve, the at least one electrode having an electrode surface axial length; and two end insulating elements, fixed to the housing such that the at least one electrode is between the end insulating elements, the end insulating elements shaped so as to define, upon placement of the housing, a nerve axial distance between the end insulating elements that is less than the electrode surface axial length.

For some applications, the electrode surface axial length is between 1.5 and 5 times the nerve axial distance.

For some applications, the end insulating elements are fixed to the housing so as to define a characteristic closest end insulating element distance to a surface of the nerve that is less than 0.5 mm. For some applications, the end insulating elements are adapted to be in physical contact with the nerve after placement of the housing.

There is also provided, in accordance with an embodiment of the present invention, apparatus for applying current to a nerve, including:

a housing, adapted to be placed in a vicinity of the nerve;

at least one electrode, fixed to the housing such that the at least one electrode does not come in direct physical contact with the nerve; and two end insulating elements, fixed to the housing such that the at least one electrode is between the end insulating elements, wherein at least one of the end insulating elements is shaped so as to define a rough surface that is adapted to be in physical contact with the nerve when the housing is placed in the vicinity of the nerve.

There is further provided, in accordance with an embodiment of the present invention, apparatus for applying current to a nerve, including:

a housing, adapted to be placed in a vicinity of the nerve;

at least one electrode, fixed to the housing such that the at least one electrode does not come in direct physical contact with the nerve; and two end insulating elements, fixed to the housing such that the at least one electrode is between the end insulating elements, at least one of the end insulating elements shaped so as to define a contact surface between the end insulating element and the nerve, wherein the contact surface is configured so as to promote connective tissue growth between the nerve and the contact surface.

For some applications, the contact surface is configured so as to promote the connective tissue growth in such a manner so as to provide insulation between the nerve and the contact surface.

For some applications, the contact surface is treated with a growth factor that can promote the connective tissue growth. Alternatively or additionally, the contact surface includes a mesh that is adapted to promote the connective tissue growth.

There is still further provided, in accordance with an embodiment of the present invention, apparatus for applying current to a nerve, including:

a housing, adapted to be placed in a vicinity of the nerve, the housing shaped so as to define an internal surface and an external surface, which external surface is configured to promote growth of fibrous connective tissue therearound; and at least one electrode, fixed to the internal surface of the housing.

For some applications, the external surface is shaped so as to define a rough surface. Alternatively or additionally, the external surface is treated with a growth factor that can promote the connective tissue growth. Further alternatively or additionally, the external surface includes a mesh that is adapted to promote the connective tissue growth.

There is additionally provided, in accordance with an embodiment of the present invention, apparatus for applying current to a nerve, including:

a housing, adapted to be placed in a vicinity of the nerve, the housing shaped so as to define an outer surface having one or more holes therethrough, which are configured to allow passage of biological materials therethrough; and one or more electrodes, fixed to the housing.

For some applications, the housing is shaped so as to define first and second chambers when the housing is placed in the vicinity of the nerve; the electrodes include an anode and a cathode, one of which is fixed to the housing within the first chamber, and the other of which is fixed to the housing within the second chamber; and the housing is shaped so as to define the one or more holes through to the first chamber, and not through to the second chamber.

There is yet additionally provided, in accordance with an embodiment of the present invention, apparatus for applying current to a nerve having a radius, the apparatus including:

a housing, adapted to be placed in a vicinity of the nerve;

first and second anodes, fixed to the housing; and a cathode, fixed to the housing between the first and the second anodes so as to define a first distance between a longitudinal center of the first anode and a longitudinal center of the cathode, and a second distance between a longitudinal center of the second anode and the longitudinal center of the cathode, the first and the second distances each at least 1 times the radius of the nerve, the housing being configured such that circumferentially symmetric current is applied by at least one electrode selected from the set consisting of: the cathode, the first anode, and the second anode.

For some applications, the first and second distances are each at least 1.5 times the radius of the nerve. For some applications, the first and second distances are each at least 2 times the radius of the nerve.

For some applications, the housing is shaped to define first, second, and third chambers, the first chamber including therein the first anode, the second chamber including therein the cathode, and the third chamber including therein the second anode.

For some applications, the housing is shaped to define at least one chamber, the chamber including therein an electrode selected from the set consisting of: the cathode, the first anode, and the second anode, and the at least one chamber is shaped to surround more than 180 degrees of a circumference of the nerve. For some applications, the electrode in the chamber is shaped to surround more than 180 degrees of the circumference of the nerve. Alternatively, the electrode in the chamber is shaped to surround less than or equal to 180 degrees of the circumference of the nerve.

There is also provided, in accordance with an embodiment of the present invention, a method, including:
providing insulating elements at two longitudinal insulation sites of a nerve;
promoting connective tissue growth between the nerve and at least one of the insulating elements; and
applying an electrical current to the nerve from at least one current application site that is not in direct physical contact with the nerve, the current application site longitudinally between the insulation sites.

There is further provided, in accordance with an embodiment of the present invention, a method including:
placing a housing in a vicinity of a nerve, the housing shaped so as to define an internal surface and an external surface;
configuring the external surface to promote growth of fibrous connective tissue therearound; and
applying an electrical current to the nerve from at least one site in a vicinity of the internal surface of the housing.

There is still further provided, in accordance with an embodiment of the present invention, a method including:
placing a housing in a vicinity of a nerve;
configuring the housing to allow passage of biological materials therethrough; and
applying an electrical current to the nerve from at least one site within the housing.

For some applications, the housing is shaped so as to define first and second chambers when the housing is placed in the vicinity of the nerve; applying the current includes applying an anodal current from within one of the chambers, and applying a cathodic current from within the other of the chambers; and configuring the housing includes configuring the housing to allow passage therethrough of biological materials to the first chamber, and not to the second chamber.

There is also provided, in accordance with an embodiment of the present invention, a method for applying current to a nerve having a radius, the method including:
applying first and second anodal currents in a vicinity of respective anodal longitudinal sites of the nerve;
applying a cathodic current in a vicinity of a cathodic longitudinal site of the nerve that is between the first and the second anodal longitudinal sites, locations of the sites defining: (a) a first distance, that is between a longitudinal center of the first anodal longitudinal site and a longitudinal center of the cathodic longitudinal site, and (b) a second distance, that is between a longitudinal center of the second anodal longitudinal site and the longitudinal center of the cathodic longitudinal site, the first and the second distances each at least 1 times the radius of the nerve; and
configuring a source of at least one current selected from the set consisting of: the cathodic current, the first anodal current, and the second anodal current, to apply the selected current as a circumferentially symmetric current.

There is further provided, in accordance with an embodiment of the present invention, apparatus for applying current to a nerve having a radius, the apparatus including:
a housing, adapted to be placed in a vicinity of the nerve;
first and second anodes, fixed to the housing; and
a cathode, fixed to the housing between the first and the second anodes so as to define a first distance between a longitudinal center of the first anode and a longitudinal center of the cathode, and a second distance between a longitudinal center of the second anode and the longitudinal center of the cathode, the first and the second distances each at least 1 times the radius of the nerve,
wherein the housing is shaped to define at least one chamber, the chamber including therein an electrode selected from the set consisting of: the cathode, the first anode, and the second anode, and
wherein the at least one chamber is shaped to surround more than 180 degrees of a circumference of the nerve.

For some applications, the electrode in the chamber is shaped to surround more than 180 degrees of the circumference of the nerve. Alternatively, the electrode in the chamber is shaped to surround less than or equal to 180 degrees of the circumference of the nerve.

For some applications, the first and second distances are each at least 1.5 times the radius of the nerve, such as at least 2 times the radius of the nerve.

For some applications, the housing is shaped to define first, second, and third chambers, the first chamber including therein the first anode, the second chamber including therein the cathode, and the third chamber including therein the second anode.

There is still further provided, in accordance with an embodiment of the present invention, a method for applying current to a nerve having a radius, the method including:
applying first and second anodal currents in a vicinity of respective anodal longitudinal sites of the nerve;
applying a cathodic current in a vicinity of a cathodic longitudinal site of the nerve that is between the first and the second anodal longitudinal sites, locations of the sites defining: (a) a first distance, that is between a longitudinal center of the first anodal longitudinal site and a longitudinal center of the cathodic longitudinal site, and (b) a second distance, that is between a longitudinal center of the second anodal longitudinal site and the longitudinal center of the cathodic longitudinal site, the first and the second distances each at least 1 times the radius of the nerve; and
configuring a source of at least one current selected from the set consisting of: the cathodic current, the first anodal current, and the second anodal current, to apply the selected current from within a chamber that surrounds more than 180 degrees of a circumference of the nerve.

There is also provided, in accordance with an embodiment of the present invention, apparatus including an implantable tubular cuff for application to a nerve, which includes:
an outer insulating wall, which includes a first flexible resilient material;
two electrodes fixed to the wall; and
an internal insulating element fixed to the wall between the two electrodes, which insulating element includes a second flexible resilient material having a hardness different from a hardness of the first material.

For some applications, the first material has a Shore D hardness of between 40 and about 50, and the second material has a Shore D hardness of between 5 and about 20.

For some applications, the insulating element is configured to come in physical contact with the nerve when the cuff is applied to the nerve.

The present invention will be more fully understood from the following detailed description of the embodiments thereof, taken together with the drawings, in which:

BRIEF DESCRIPTION OF THE DRAWINGS

FIG. 7 is a graph modeling a calculated activation function over a portion of the length of a nerve to which current is applied using an electrode assembly such as that shown in FIG. 2A, in accordance with an embodiment of the present invention;

FIGS. 8 and 9 are schematic pictorial illustrations of a tubular cuff in a slightly opened position and a closed position, respectively, in accordance with an embodiment of the present invention;

FIG. 10 is a cross-sectional view of the cuff of FIGS. 8 and 9 in a closed position in the plane A-A of FIG. 9, in accordance with an embodiment of the present invention;

FIG. 11 is a cross-sectional view of a protrusion of the cuff of FIGS. 8 and 9, in accordance with an embodiment of the present invention;

FIG. 12 is a cross-sectional view of another tubular cuff in a slightly opened position, in accordance with an embodiment of the present invention;

FIGS. 17, 18, and 19 are schematic, cross-sectional illustrations of electrode cuffs, in accordance with respective embodiments of the present invention;

DETAILED DESCRIPTION OF EMBODIMENTS

Figure 1A:
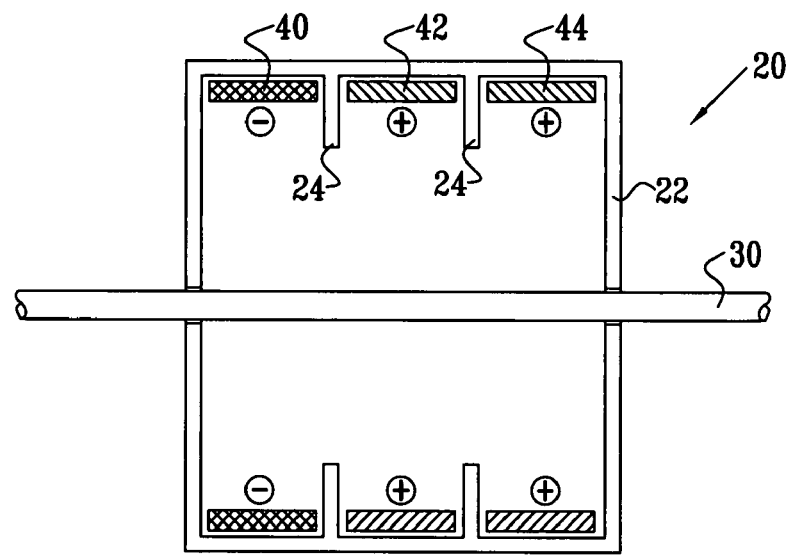
FIG. 1A is a schematic, cross-sectional illustration of an electrode assembly for applying current to a nerve, in accordance with an embodiment of the present invention.
Figure 1B:
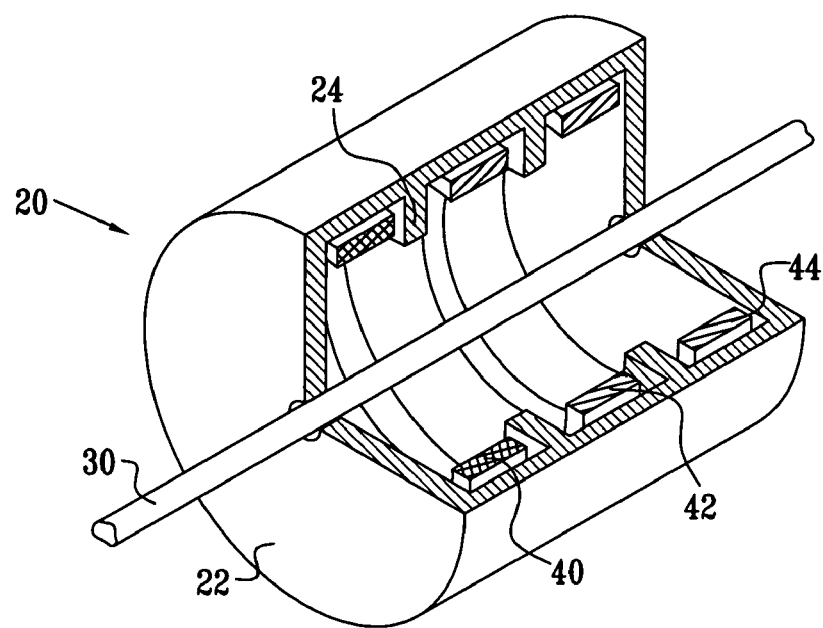
FIG. 1B is a schematic pictorial illustration of the electrode assembly of FIG. 1A, in accordance with an embodiment of the present invention.

Reference is now made to FIGS. 1A and 1B. FIG. 1A is a schematic, cross-sectional illustration of an electrode assembly 20 for applying current to a nerve 30, in accordance with an embodiment of the present invention. FIG. 1B is a schematic pictorial illustration of electrode assembly 20, in accordance with an embodiment of the present invention. It is noted that although the various electrode assemblies shown in the figures generally contain cylindrical configurations of their elements, other geometrical configurations, such as non-rotationally symmetric configurations, are also suitable for applying the principles of the present invention. In particular, a housing 22 of the electrode assembly (and the electrodes themselves) may form a complete circle around the nerve, or it may define an arc between approximately 0 and 90 degrees, between 90 and 180 degrees, between 180 and 350 degrees, or between 350 and 359 degrees around the nerve. (One such embodiment, shown in FIG. 1B, includes the housing and the electrodes defining an arc of 270 degrees.)

Typically, the electrode assembly comprises a cathode 40, a primary inhibiting anode 42, and a secondary inhibiting anode 44. Each of these electrodes is fixed within housing 22 of the electrode assembly. Insulating elements 24, which are typically either part of the body of the housing or affixed thereto, are typically placed so as to separate the electrodes, and to guide current from one of the electrodes towards the nerve prior to being taken up by another one of the electrodes. Typically (as shown), the insulating elements are closer to nerve 30 than are the electrodes. Alternatively (not shown), insulating elements 24 are generally flush with the faces of the electrodes.

Typically, cathodic current driven through cathode 40 by a control unit (not shown) stimulates fibers within nerve 30 to generate action potentials which travel in both directions within the nerve—i.e., towards anodes 42 and 44 ("the anodal direction"), and in the opposite direction, out of housing 22, towards a target ("the target direction"). Anodal current driven through anode 42, by contrast, is typically applied so as to inhibit the action potentials which were induced by the cathodic current, and which subsequently traveled in the anodal direction.

For most applications, current applied by secondary inhibiting anode 44 is of lower magnitude than the current applied by primary inhibiting anode 42. In this manner, the "virtual cathode" effect induced by the primary anodal current is minimized. In accordance with an embodiment of the present invention, application of the primary and secondary anodal currents in appropriate ratios is configured to generally minimize the virtual cathode effect. Typically, but not necessarily, the ratio of the primary to the secondary anodal current ranges from 2:1 to 10:1.

Figure 2A:
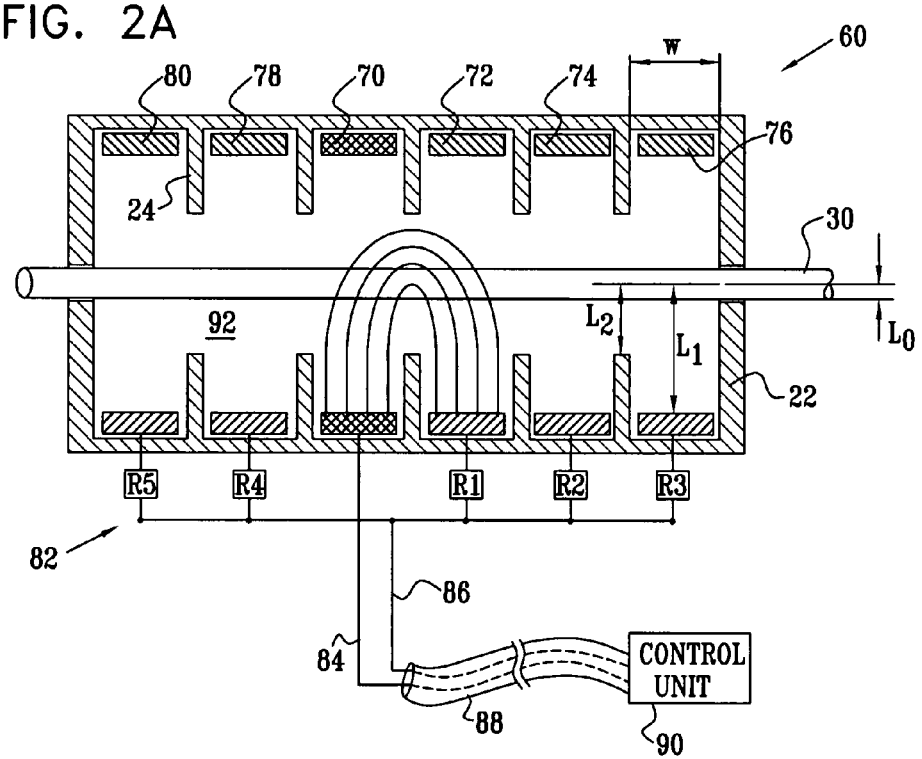
FIGS. 2A and 2B are schematic, cross-sectional illustrations of other electrode assemblies for applying current to a nerve, in accordance with respective embodiments of the present invention.

FIG. 2A is a schematic, cross-sectional illustration of an electrode assembly 60, in accordance with another embodiment of the present invention. Electrode assembly 60 comprises a cathode 70, a primary inhibiting anode 72, and a secondary inhibiting anode 74, which are typically driven in a manner analogous to that described hereinabove with respect to cathode 40 and primary and secondary inhibiting anodes 42 and 44.

Typically, electrode assembly 60 additionally comprises a tertiary anode 76, which is employed to reduce any virtual cathode effect which may be induced by secondary inhibiting anode 74. For example, relative to a normalized cathodic current of −1, the primary inhibiting anode, secondary inhibiting anode, and tertiary anode may be configured to apply respective currents of 0.66, 0.25, and 0.09. Typically, the magnitude of the current from the tertiary anode is sufficiently small, such that the virtual cathode effect resulting therefrom does not generate action potentials that interfere with the performance of electrode assembly 60. For some applications, however, particularly when the current from primary inhibiting anode 72 is relatively high, additional anodes (not shown) are provided in electrode assembly 60.

Electrode assembly 60 typically comprises a primary fiber-selection anode 78, adjacent to cathode 70 and on the other side of the housing from anodes 72, 74, and 76. The current applied by cathode 70 typically induces bi-directional action potential propagation in fibers in nerve 30 having a range of diameters. In order to block propagation past anode 78 of those action potentials traveling in relatively larger fibers, the primary fiber-selection anode is typically driven to apply anodal current configured to block action potential propagation in these larger fibers of nerve 30, and configured not to block action potential propagation in the smaller fibers. In particular, since the larger fibers are generally more sensitive to being blocked by a lower level of anodal current than are the smaller fibers, a given level of current applied through fiber-selection anode 78 typically blocks action potentials in the larger fibers, while allowing passage of action potentials induced by the current from cathode 70 and traveling in the small fibers. Therefore, action potentials induced by the cathode continue to propagate in the smaller fibers, past primary fiber-selection anode 78, out of housing 22, and towards a target site. By increasing the current driven through the primary fiber-selection anode, progressively smaller fibers are inhibited from propagating action potentials. Conversely, by decreasing the application of current through primary fiber-selection anode 78, larger fibers are able to propagate action potentials.

For applications in which the current applied through primary fiber-selection anode 78 is sufficient to create a substantial virtual cathode effect, a secondary fiber-selection anode 80 is typically incorporated into electrode assembly 60, adjacent to the primary fiber-selection anode and on the far side of cathode 70. In a fashion analogous to that described hereinabove with respect to secondary inhibiting anode 74, secondary fiber-selection anode 80 is typically driven to apply a current to the nerve smaller than that applied by primary fiber-selection anode 78, so as to counteract the virtual cathode effect which would otherwise, in some circumstances, induce action potential propagation responsive to the current applied by primary fiber-selection anode 78.

Typically, fixed ratios for the currents applied by anodes 72, 74, 76, 78, and 80 are pre-defined and are set in hardware, e.g., by a set 82 of resistors R1, R2, R3, R4, and R5, which couple a single lead 86 coming from a control unit 90 to the respective anodes. Typically, a guide tube 88 conveys lead 86, in combination with a second lead 84 that drives cathode 70, from control unit 90 to electrode assembly 60. Advantageously, this embodiment provides control over multiple anodes, and corresponding reduction of the virtual cathode effect, with a minimum number of leads.

Alternatively, for some applications (not shown), particularly when cathodic and anodal current parameters vary over a wide range, the various anodes are independently driven by the control unit via respective leads, so as to optimize the minimization of the virtual cathode effect and the maximization (when appropriate) of anodally-induced hyperpolarization. For some applications, a combination of the two techniques described are utilized, whereby, for example, anodes 72, 74, and 76 are driven by current in a single lead, and anodes 78 and 80 are driven by current in two additional, separate leads.

Typically, electrode assembly 60 (as well as the other electrode assemblies described herein, as appropriate) has physical dimensions configured so as to provide a relatively uniform activation function across the cross-section of nerve 30. The distance L1 separating the central longitudinal axis of nerve 30 from cathode 70 and from anodes 72, 74, 76, 78, and 80 is typically at least approximately 1.5 times greater than the radius L0 of the nerve. For many applications, L1 is greater than two times L0. By placing the cathode and anodes at such distances, increased electrical field uniformity is obtained within the nerve, particularly as the gradients in the activation function are largest near the electrodes, and are significantly reduced across the cross-section of the nerve. This, in turn, increases the ability of control unit 90 to assure that most fibers within the nerve will experience generally the same level of applied currents.

Insulating elements 24 typically separate cathode 70 from anodes 72 and 78. For some applications, additional insulating elements 24 separate the various adjacent anodes in electrode assembly 60. The insulating elements define a characteristic closest "insulating element distance" L2 to the axis of nerve 30 that is typically at least approximately 1.5 times greater than L0. It will be appreciated that for structural reasons, spokes or other offshoots of the insulating elements may come closer to the nerve. However, the "functional" portions of the insulating elements, i.e., those portions which provide a substantial effect on the direction of current flow between the electrodes and through the nerve, typically remain at a closest distance L2 of at least 1.5*L0. For some applications, particularly those in which battery life is a pressing factor, L2 is set to be less than 1.5*L0, at the expense of some uniformity of the applied field.

Typically, L1 is greater than or equal to L2. For anode and cathode widths W, typical values for L1 are in the range L2<L1<1.5 (L2+w), e.g., L2+0.5 w<L1<L2+w. Typically, the width w of the electrodes is approximately equal to 0.5*L0. (The width w, as well as other dimensions, are not drawn to scale in the figures.) In accordance with an embodiment of the present invention, when L0 is between 1 and 2 mm, L2 is typically between 1.5 and 3 mm, L1 is between 1.5 and 4 mm, and w is between 0.5 and 1 mm.

Figure 2B:
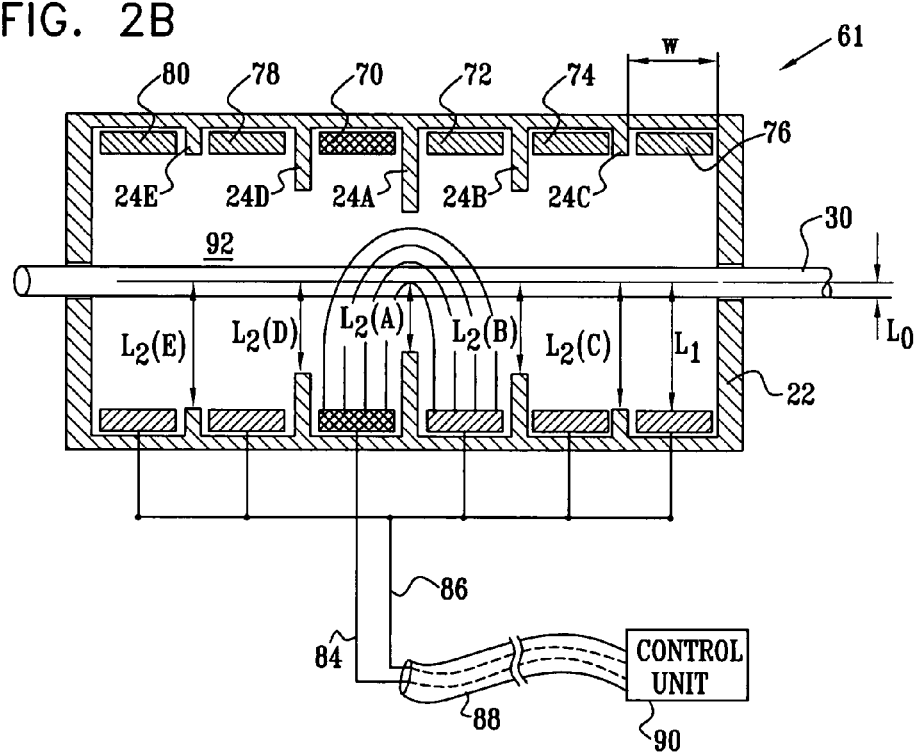

FIG. 2B is a schematic, cross-sectional illustration of an electrode assembly 61, in accordance with another embodiment of the present invention. Electrode assembly 61 is generally similar to electrode assembly 60, described hereinabove with reference to FIG. 2A, except for differences as described.

Whereas in electrode assembly 60, insulating elements 24 all had generally equal dimensions, electrode assembly 61 provides each of five insulating elements 24A, 24B, 24C, 24D, and 24E with a respective (typically different) distance to the axis of nerve 30 of L2(A), L2(B), L2(C), L2(D), and L2(E). In general, as the distance L2($x$) for any given one of the insulating elements decreases, the current density experienced by the nerve in a vicinity of the insulating element increases. Thus, for example, in the embodiment shown in FIG. 2B, L2(C) corresponding to insulating element 24C is relatively large, such that the current density in the nerve near anode 76 is low.

Figure 3A:
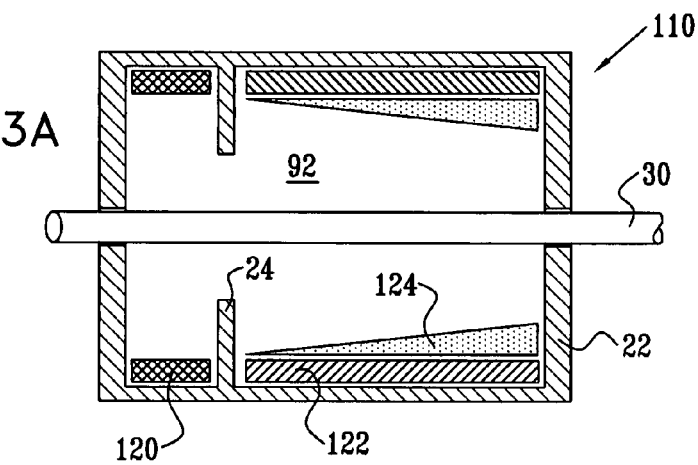
FIGS. 3A, 3B, and 3C are schematic, cross-sectional illustrations of yet other electrode assemblies for applying current to a nerve, in accordance with respective embodiments of the present invention.

FIG. 3A is a schematic, cross-sectional illustration of an electrode assembly 110, in accordance with an embodiment of the present invention. Electrode assembly 110 is analogous to electrode assembly 20, described hereinabove with reference to FIG. 1A, except for differences as described. A cathode 120 of electrode assembly 110 serves generally the same purpose as cathode 40, while an elongated anode 122 typically replaces anodes 42 and 44. Typically, elongated anode 122 is 0.5 mm-10 mm in length, although it may be longer or shorter responsive to the level of currents expected to be applied therethrough.

Elongated anode 122, when placed on or over nerve 30, typically has at least two levels of electrical impedance associated therewith, between respective sites on the elongated anode and the nerve. A biological material 92, typically including fibrous tissue and body fluids, generally occupies some of the space between the electrodes and the nerve. The impedance governing the passage of current from elongated anode 122 to nerve 30 is therefore typically a function of the properties of biological material 92. Additionally, a resistive element 124 (e.g., a shaped iridium oxide coating, a titanium nitride coating, or a platinum iridium coating) typically provides greater electrical impedance distal to cathode 120 than proximal thereto. In an embodiment, the coating undergoes a surface treatment (e.g., "sand blasting" or a chemical treatment), in which the effective microscopic surface area is increased by the treatment. Typically, the proximal-to-the-cathode end of the coating is more heavily treated by the surface treatment, and therefore has lower impedance. Alternatively or additionally, the geometry of the elongated anode is configured so as to effect the change in impedance as described.

Typically, the anodal current leaving the portion of elongated anode 122 distal to cathode 120 minimizes the virtual cathode effect induced thereat by anodal current leaving the portion of elongated anode 122 proximal to cathode 120.

Figure 3B:
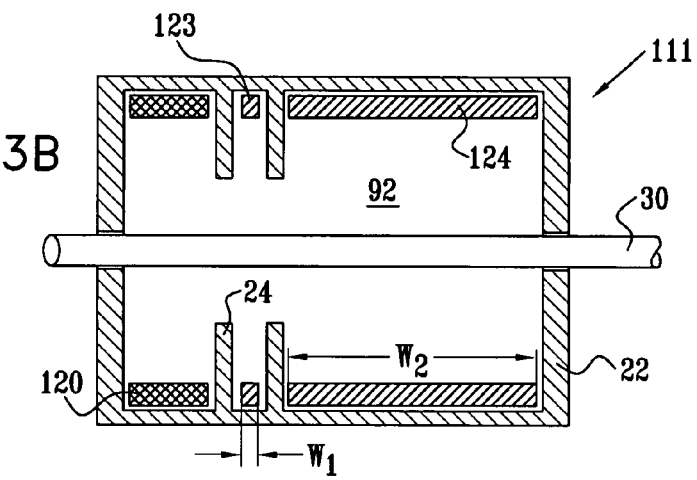

FIG. 3B is a schematic, cross-sectional illustration of an electrode assembly 111, in accordance with an embodiment of the present invention. Typically, a current density in a vicinity of a primary anode 123 is higher than a current density in a vicinity of a secondary anode 124. The difference in current densities is typically attained by having a width w2 of anode 124 be at least 2-10 times higher than a corresponding width w1 of anode 123. In this manner, when generally the same current is passed through both anodes, the current density—and thus the hyperpolarizing effect on the activation function—is greater near anode 123 than near anode 124.

Figure 3C:
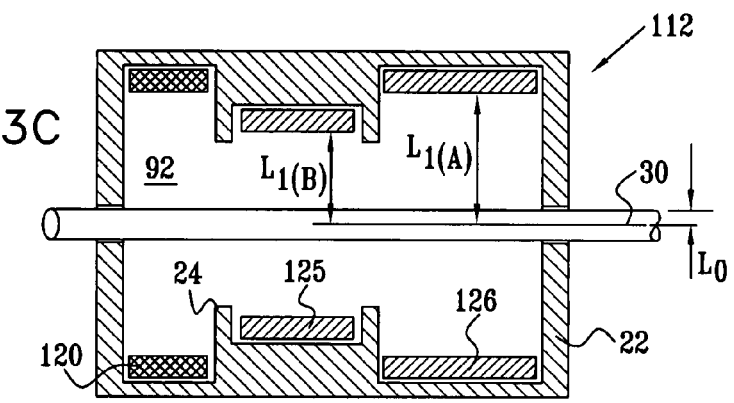

FIG. 3C is a schematic, cross-sectional illustration of an electrode assembly 112, in accordance with an embodiment of the present invention. In this embodiment, the distance L1(B) between a primary anode 125 and the axis of nerve 30 is typically smaller than the distance L1(A) between a secondary anode 126 and the axis of the nerve. The distance of cathode 120 from the axis is similar to L1(A) (as shown), while in other embodiments (not shown) the distance is closer to L1(B). In a manner similar to that described with reference to FIG. 3B, the geometrical configuration of the cathode and the anodes shown in FIG. 3C typically provides higher current density near the anode that is proximal to the cathode, and provides generally lower current density near the anode that is distal to the cathode.

Figure 4:
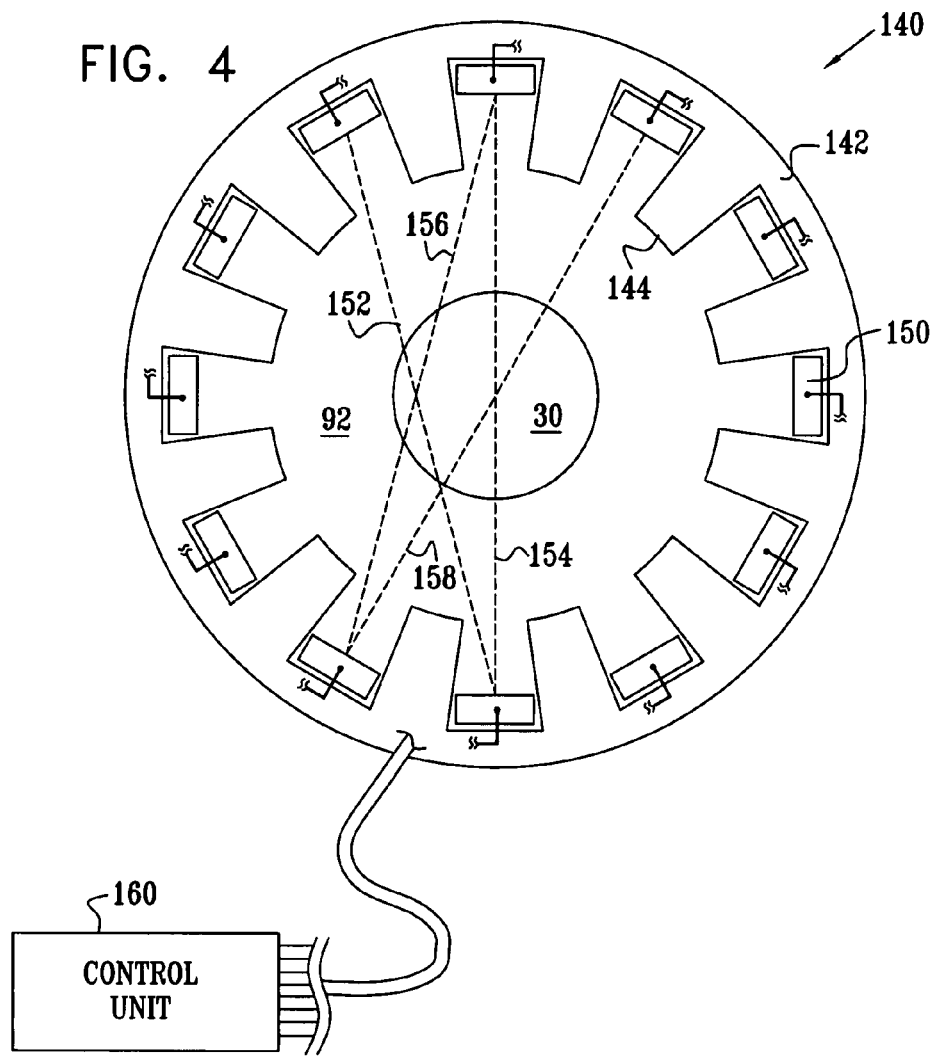
FIG. 4 is a schematic, cross-sectional illustration of still another electrode assembly for applying current to a nerve, in accordance with an embodiment of the present invention.

FIG. 4 is a schematic, cross-sectional illustration of an electrode assembly 140 surrounding nerve 30, which is driven by a control unit 160 to apply current to the nerve, in accordance with an embodiment of the present invention. Two or more electrodes 150 fixed to a housing 142 are placed at respective positions around the axis. Typically, electrodes 150 comprise at least three, and typically four or more electrodes. In this case, insulating elements 144 are typically disposed between adjacent electrodes. If there are only two electrodes, then control unit 160 typically alternates the direction of the current driven between the two electrodes at a rate greater than 1000 Hz.

When there are three or more electrodes 150, thereby defining a ring of electrodes, control unit 160 typically cycles its driving of the electrodes in accordance with a stimulation protocol. For example, one such protocol for three electrodes may include driving current between electrodes 1 and 2, then 2 and 3, then 3 and 1, then 1 and 2, etc., cycling through the combinations at an average rate of greater than 1000 Hz, or, for some applications, greater than 10,000 Hz. For larger numbers of electrodes, e.g., 6, 12, or 24, the stimulation cycling protocol is typically more complex, and is typically configured to cause current to pass through or close to most or all fibers in the nerve at the longitudinal site where the ring of electrodes is placed. One such complex protocol includes effectively creating a star out of successive current lines passing through the nerve. In FIG. 4, an initial set of four such lines 152, 154, 156, and 158 are shown.

Figure 5:
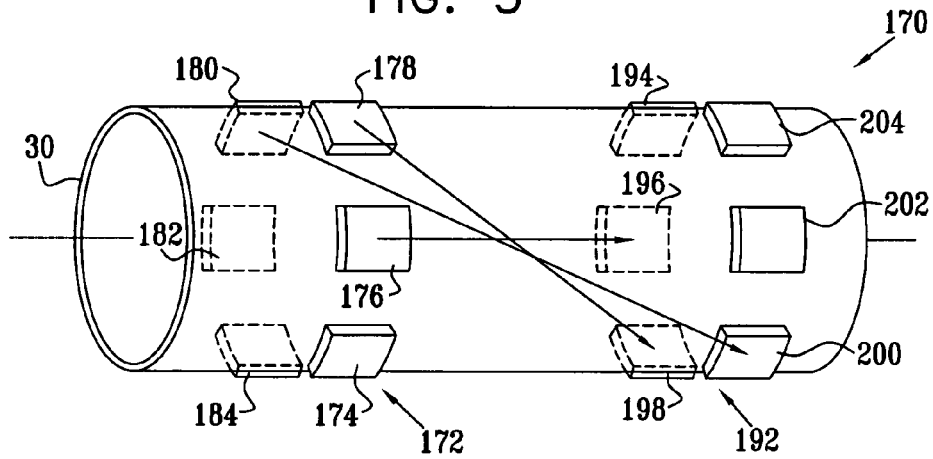
FIG. 5 is a schematic, pictorial illustration of an additional electrode assembly for applying current to a nerve, in accordance with an embodiment of the present invention.

FIG. 5 is a schematic, pictorial illustration of an electrode assembly 170, in accordance with another embodiment of the present invention. Electrode assembly 170 comprises an anodal ring 172 of two or more anodes and a cathodic ring 192 of two or more cathodes. In the embodiment shown in FIG. 5, anodal ring 172 comprises anodes 174, 176, 178, 180, 182, and 184, and cathodic ring 192 comprises cathodes 194, 196, 198, 200, 202, and 204. Each ring of electrodes is placed around the nerve axis, at a respective anodal or cathodic longitudinal site of the nerve.

Typically, a control unit drives anode 176 to drive current through nerve 30 to cathode 196, in order to initiate generation of action potentials near cathode 196 and/or near a substantial portion of cathodic ring 192. Cathode 196 and anode 176 are typically at mutually-opposed orientations with respect to the axis. In this manner, a greater portion of the current from anode 176 enters nerve 30 than if, for example, the control unit were to drive anode 176 to send the same amount of charge to cathode 202. In this latter case, a substantial portion of the current leaving anode 176 would travel directly through the biological material surrounding nerve 30, and not enter into nerve 30.

In the example shown in FIG. 5, after anode 176 sends current to cathode 196, anode 178 sends current to cathode 198, and then anode 180 sends current to cathode 200. Typically, an entire sweep of all of the electrodes in the two rings is accomplished within 0.01-1 millisecond.

Advantageously, by utilizing discrete electrodes arranged into a ring of cathodes and a ring of anodes, each located at respective longitudinal sites on the nerve, fibers in the nerve are stimulated near the ring of cathodes, and inhibited near the ring of anodes, typically using substantially less current than if a solid anode ring and a solid cathode ring were placed around the nerve. Further advantageously, steering of current to traverse or avoid certain regions in the cross-section of the nerve is readily attainable, using the techniques described herein, by suitable activation of the cathodes and/or anodes.

For simplicity, FIG. 5 shows only a single anodal ring 172. It is noted that the use of rings of anodes and/or a ring of cathodes is typically also applied, as appropriate, in combination with the cathode-anode-anode configuration of FIGS. 1A and 1B, or in combination with the anode-anode-cathode-anode-anode-anode configuration of FIGS. 2A and 2B. In an embodiment, some of the electrodes (e.g., cathode 70 and anodes 72 and 78) comprise multiple electrodes disposed in a ring, while others of the electrodes (e.g., anodes 74, 76, and 80) are generally solid rings, each comprising only a single ring.

Figure 6:
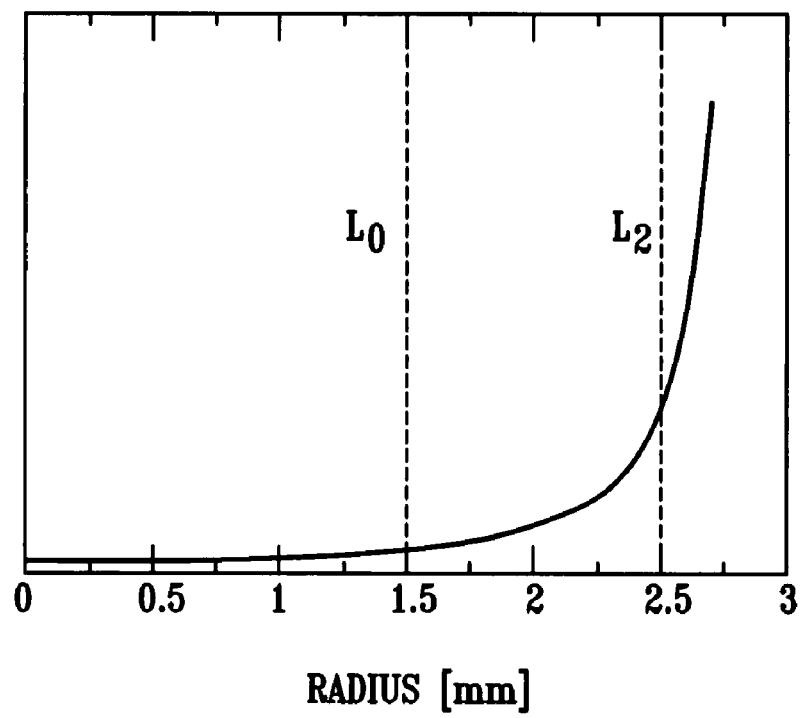
FIG. 6 is a graph modeling a calculated activation function over a range of distances from the central axis of a nerve to which current is applied using an electrode assembly such as that shown in FIG. 1A, in accordance with an embodiment of the present invention.

FIG. 6 is a graph modeling calculated activation function over a range of distances from the central axis of a nerve, in accordance with an embodiment of the present invention. The graph models, in a simplified fashion, the activation function, at a cathodic site, produced in response to application of current by, for example, electrode assembly 20 (FIG. 1A) or electrode assembly 60 (FIG. 2A). The equation producing the graph shown in FIG. 6 is:

$$AF(r) = \frac{1}{2\pi} \int_0^{2\pi} \left[ 1 + \left(\frac{r}{R}\right)^2 - 2\left(\frac{r}{R}\right)\cos\varphi \right]^{-1.5} d\varphi,$$

where r is the radius from the central axis of the nerve, and R is the distance of an electrode ring from the axis. L0 in the figure shows the radius of a typical nerve, and L2 shows the distance to an insulating element. As noted above, the amount of change of the activation function within the nerve (r<L0) is significantly smaller than the amount of change of the activation function outside the nerve (r>L0).

FIG. 7 is a graph modeling calculated activation function over a portion of the length of nerve 30, when current is applied using an electrode assembly such as that shown in FIG. 2A (without applying current through anodes 78 and 80), in accordance with an embodiment of the present invention. For the purposes of modeling the activation function, cathode 70 is placed at a longitudinal site on the nerve labeled z=−3 (in relative units), and anodes 72, 74, and 76 are placed at longitudinal positions z=0, 1.4, and 2.7. Anodes 72, 74, and 76 are driven to apply currents A1=0.66, A2=0.25, and A3=0.09, respectively. Each one of the electrodes generates its own activation function responsive to the applied currents, as modeled in FIG. 7.

The top three data lines in FIG. 7 show that each of the anodes generates a depolarization portion (most clearly seen for applied current A1) and a hyperpolarization portion (clearly seen for each anode). It is noted that the depolarization portion of the activation function generated by the largest applied anodal current (A1) at approximately z=1.2 is substantial, and, in many cases, is sufficient to stimulate fibers within the nerve.

The sum of the effect of each of the anodal activation functions is seen in the fourth data line in FIG. 7, labeled "summed anodes." This line demonstrates that the hyperpolarization portion of the activation function due to anodal current A2 significantly counteracts the depolarization portion of the activation function due to anodal current A1. Advantageously, the peaks 222 at z>0 are generally not of sufficient magnitude to excessively stimulate the nerve fibers within nerve 30 by means of the virtual cathode effect. Nevertheless, the maximum hyperpolarization peak 220 of the "summed anodes" curve remains strong, sufficient to inhibit action potential propagation in a substantial proportion of the fibers of nerve 30. The ratio of the magnitude of peak 220 to the magnitude of the highest of depolarization peaks 222 is typically at least 8:1, and is typically greater than 10:1.

The bottom data line in FIG. 7 shows the combined effect on the activation function due to the summed anode activation function and the activation function due to the cathode. It is noted that the use of the various anodes does not excessively decrease either the magnitude of the desired depolarizing peak 230, or that of the desired hyperpolarizing peak 240 of the combined activation function.

Reference is now made to FIGS. 8 and 9, which are schematic pictorial illustrations of a tubular cuff 300 in a slightly opened position and a closed position, respectively, in accordance with an embodiment of the present invention. For some applications, such as those described hereinabove or in the patent applications referenced hereinbelow, cuff 300 is adapted to surround and enclose a nerve of a subject. Alternatively, cuff 300 is adapted to surround and enclose other generally tubular tissue of the subject, such as a blood vessel, a muscle, a tendon, a ligament, an esophagus, intestine, or a fallopian tube. For example, cuff 300 may be placed around a blood vessel in order to prevent rupture of an aneurysm.

Cuff 300 defines a central lumen 304 and a longitudinal slit 306, as best seen in FIG. 8. A first edge 308 of the cuff is brought in contact with a second edge 310 thereof in order to close the cuff around tubular tissue passing through lumen 304. Cuff 300 defines one or more holes 312 passing therethrough, in a vicinity of first edge 308, as seen in FIG. 8. In a vicinity of second edge 310, the cuff comprises one or more protrusions 314, generally corresponding to the number of holes 312. When protrusions 314 are passed through respective holes 312, the protrusions engage the holes, thereby closing the cuff around the tubular tissue. Cuff 300 typically may be repeatedly opened and closed by a surgeon. The number of protrusions and holes which cuff 300 comprises depends on the length of the cuff and the specific application. For example, when cuff 300 has a length of about 1 cm and is adapted for coupling to a nerve, the cuff typically comprises one, two, or three protrusions.

FIG. 10 is a cross-sectional view of cuff 300 in a closed position in the plane A-A of FIG. 9, in accordance with an embodiment of the present invention. In this embodiment, protrusion 314 comprises a head portion 316 and a neck portion 318, which is narrower than the head portion. To couple first edge 308 to second edge 310, head portion 316 is drawn through hole 312. Since head portion 316 and cuff 300 comprise a flexible material, as described hereinbelow, the head portion is able to be drawn through hole 312, even thought the hole is smaller than the head portion. Once the head portion emerges from the hole, the head portion and hole typically return to substantially their initial respective shapes. The head portion thus typically remains in place unless the first and second edges are deliberately drawn apart by a force greater than that which naturally occurs in the environment in which cuff 300 is typically used (e.g., surrounding a nerve or blood vessel). As can be seen in FIG. 10, when cuff 300 is in a closed position, neck portion 318 of protrusion 314 typically occupies substantially all of hole 312, and, in the plane A-A, a portion 320 of first edge 308 is separated from the remainder of first edge 310 by hole 312.

Although head portion 316, neck portion 318, and hole 312 are shown in the figures as generally rectangular in shape, this is by way of example only. In actual implementations, these elements may have various shapes, such as squares, circles, or ellipses. Additionally, these three elements need not all have the same shape; for example, the hole and neck portion may be rectangular, while the head portion is circular. Alternatively, the hole may be simply a slit in the material of the cuff, and the protrusion passes through the slit.

For use of cuff 300 with a nerve, a thickness T of the wall of cuff 300, at the wall's thinnest point, is typically between about 0.1 and 10 mm. An internal diameter D of the cuff at its widest point is typically between about 0.1 and 50 mm. Typically, a length L of hole 312 (FIG. 8) is between about 0.5 and about 5 mm, and a width W of the hole is between about 0 and about 5 mm. (It is noted that a width of 0 mm corresponds to the hole being a slit.)

Reference is again made to FIG. 9. For some applications, first edge 308 comprises a flap 322. A region of contact 324 between the inner surface of the flap and the outer surface of second edge 310 typically serves as a good mechanical and electrical seal when cuff 300 is in its closed position. This good seal generally prevents the ingrowth of tissue, which sometimes occurs when conventional cuffs are implanted on a long-term basis.

FIG. 11 is a cross-sectional view of protrusion 314, in accordance with an embodiment of the present invention. Cuff 300 comprises one or more filaments 326, such as sutures or filaments made from silicone, each of which is coupled to one of protrusions 314, typically to neck portion 318 thereof. For example, the filament may be passed around the neck portion and knotted at the time of manufacture of cuff 300, so that both ends 328 of the filament extend from the protrusion. Other techniques for attaching filament 326 to protrusion 314 will be readily apparent to those skilled in the art, having read the present patent application. For some applications, filaments 326 are an integral portion of cuff 300, such as when the filaments comprise silicone sutures and the cuff comprises silicone. In order to draw protrusion 314 through hole 312, a surgeon threads filament 326 through hole 312, and draws the filament until head portion 316 passes through the hole. Ends 328 of filament 326 may be coupled to each other in order to make the threading easier to perform. Upon completion of the surgery, the surgeon may clip off the filament. Alternatively, the filament may comprise a biodegradable material, in which case the filament can be left in place to degrade over time. In embodiments of cuff 300 that do not comprise filament 326, the surgeon typically uses standard surgical tools, such as tweezers, to draw protrusion 314 through hole 312.

FIG. 12 is a cross-sectional view of a tubular cuff 400 in a slightly opened position, in accordance with an embodiment of the present invention. Cuff 400 is generally similar to cuff 300, as described hereinabove with reference to FIGS. 8-11, except for differences described hereinbelow. Cuff 400 comprises a flap 422 set at an angle α to the surface of the cuff. The angle α is typically between 90 and 180 degrees, such as 90 degrees. Optionally, cuff 400 additionally comprises a tab 450, which a surgeon may grasp in order to assist in bringing a hole 412 over a protrusion 414 and holding the hole in place while drawing the protrusion therethrough. Tab 450 typically has a length L of between about 5 and about 25 mm. Cuff 400 typically may be repeatedly opened and closed by the surgeon.

Figure 13:
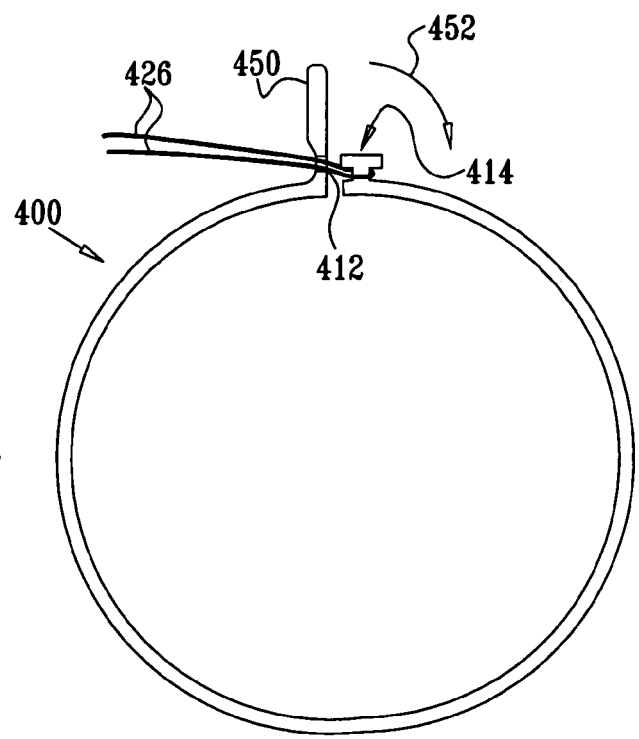
FIGS. 13 and 14 are cross-sectional views of the cuff of FIG. 12 in a slightly opened position and a closed position, respectively, in accordance with an embodiment of the present invention.
Figure 14:
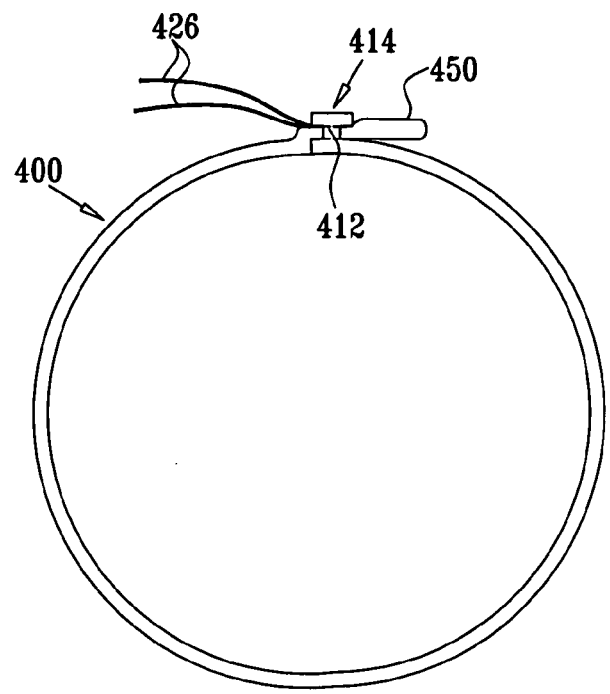

FIGS. 13 and 14 are cross-sectional views of tubular cuff 400 in a slightly opened position and a closed position, respectively, in accordance with an embodiment of the present invention. In this embodiment, cuff 400 additionally comprises a filament 426. The surgeon threads the filament through hole 412, and then grasps the filament while simultaneously moving tab 450 in generally the opposite direction, i.e., in the direction indicated by an arrow 452 in FIG. 13. As a result, protrusion 414 is drawn through hole 412, thereby closing cuff 400 around the tubular tissue.

Figure 15:
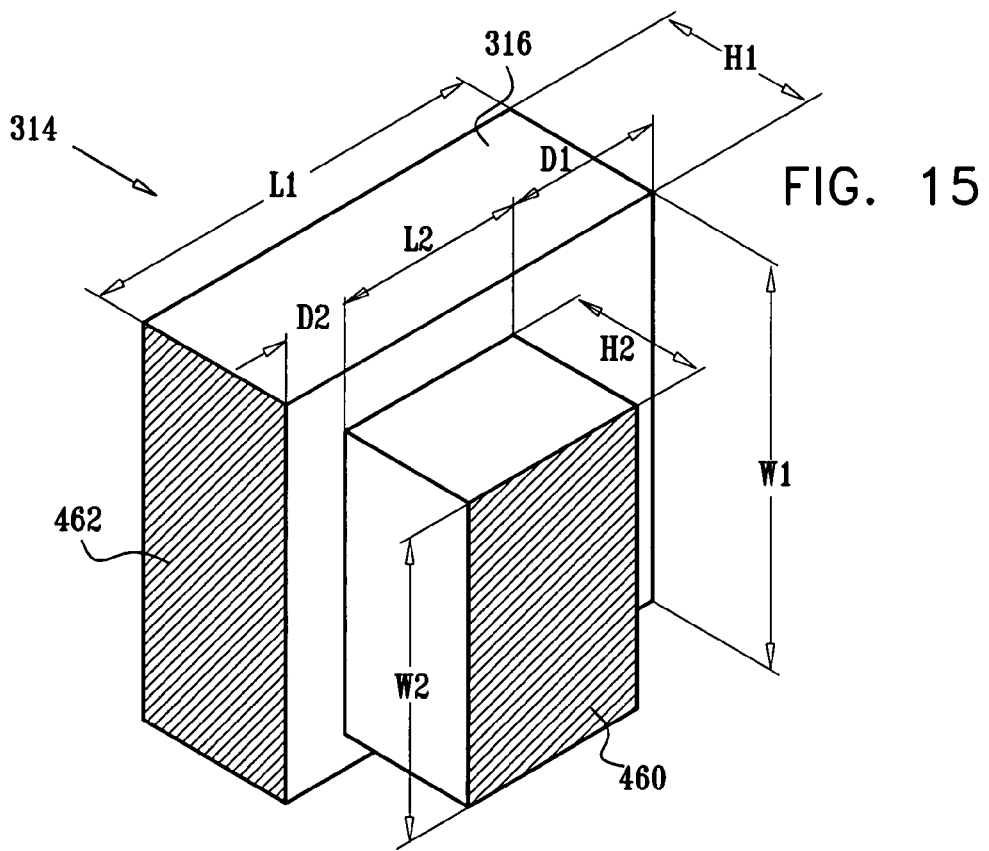
FIG. 15 is an enlarged schematic pictorial illustration of a protrusion of the cuff of FIGS. 8 and 9, in accordance with an embodiment of the present invention.

FIG. 15 is an enlarged schematic pictorial illustration of protrusion 314, in accordance with an embodiment of the present invention. A surface 460 is coupled to cuff 300 in the vicinity of second edge 310, while a surface 462 is oriented towards the second edge, as described hereinabove. Head portion 316 of the protrusion (FIGS. 10, 15) typically has a length L1 of between about 0.4 and about 8 mm, a width W1 of between about 0.4 and about 8 mm, and a height H1 of between about 0.4 and about 4 mm. Neck portion 318 of the protrusion typically has a length L2 of between about 0.4 and about 5 mm, a width W2 of between about 0.4 and about 5 mm, and a height H2 of between about 0.4 and about 4 mm. A distance D2 between neck portion 318 and surface 462 is typically between about 0% and about 200% of a distance D1 between neck portion 318 and the surface of head portion 316 opposite surface 462. Alternatively, D1 may be approximately zero.

Figure 16:
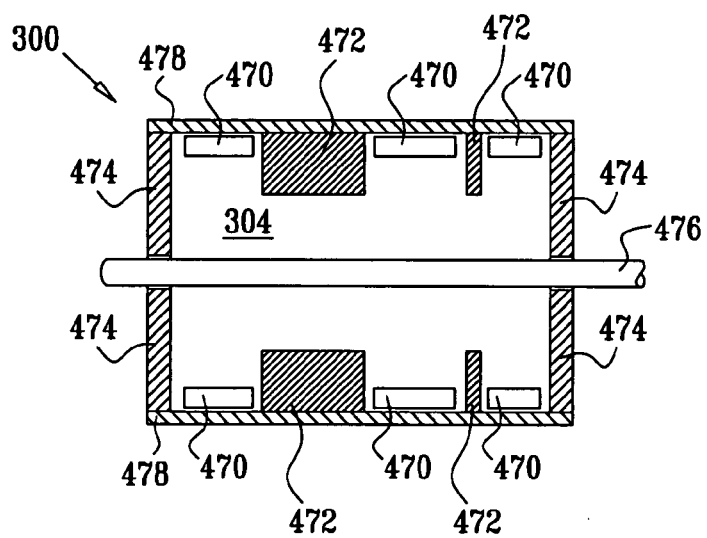
FIG. 16 is a schematic, cross-sectional illustration of the cuff of FIGS. 8 and 9 in the plane B-B of FIG. 9, in accordance with an embodiment of the present invention.

Reference is made to FIG. 16, which is a schematic, cross-sectional illustration of cuff 300 in the plane B-B of FIG. 9, in accordance with an embodiment of the present invention. Cuff 300 may comprise one or more stimulating and/or sensing electrodes 470, for example using techniques described hereinabove and/or in the patent applications referenced hereinbelow. Alternatively or additionally, cuff 300 may incorporate one or more other features of the electrode assemblies described hereinabove. For example, cuff 300 may comprise one or more internal insulating elements 472 positioned between electrodes 470. The cuff may also comprise one or more end insulating elements 474, which extend towards tubular tissue 476 in order to electrically isolate a portion of tissue 476 within lumen 304 from a portion of tissue 476 outside the cuff.

Cuffs 300 and 400 typically comprise a flexible, resilient biocompatible material, such as silicone or polyurethane. For some applications, the cuffs comprise more than one material, for example, to provide better control of diameters, thicknesses, and/or strengths of various portions of the cuff. For example, an outer wall 478 of cuff 300 (FIG. 16) may comprise a material having a Shore D hardness of between about 40 and about 50, while insulating elements 472 and/or 474 may comprise a material having a Shore D hardness of between about 5 and about 20, e.g. about 10. Such a hardness of outer wall 478 generally facilitates the safe and easy removal of fibrosis tissue that grows around the cuff. Cuffs 300 and 400 are typically manufactured by extrusion and/or injection molding. Although outer wall 478 and insulating elements 472 and 474 are shown as two separate elements in the figure, for some applications they are formed as a single integrated unit.

For some applications, electrodes 470 comprise platinum, a platinum alloy, titanium, and/or a titanium alloy. If electrode leads coupled to the electrodes comprise materials other than platinum or a platinum alloy, connections to the leads are typically made at a distance of at least 2 cm from the surface of the electrodes that are in electrical contact with tissue 476. Alternatively, electrodes 470 comprises a non-platinum material, and a connection between the non-platinum material and the leads are made at a distance of at least 2 cm from the surface of the electrodes that are in electrical contact with tissue 476.

Insulating elements 472 and 474 may be somewhat removed from tissue 476 (as shown), or, alternatively, the insulating elements may be disposed in contact or practically in contact with tissue 476. In the latter case, the insulating elements are typically adapted to be, after placement of the cuff, in physical contact with tissue 476, or substantially in physical contact with tissue 476, e.g., less than about 0.5 mm from tissue 476. Such physical or substantially physical contact typically causes current flowing through one or more electrodes 470 to pass through tissue 476, rather than partially between the insulating elements and the tissue. For some applications, the insulating elements are adapted to be in physical contact with tissue 476 immediately upon placement of the cuff. Alternatively, the insulating elements are adapted to be in physical contact with tissue 476 after a period of adaptation of the tissue to the placement of the cuff. For example, such adaptation may include swelling of tissue 476 and/or the growth of connective tissue between tissue 476 and the insulating elements.

Reference is now made to FIG. 17, which is a schematic, cross-sectional illustration of a cuff 500, in accordance with an embodiment of the present invention. Numerals in FIG. 17 refer to the same elements as corresponding numerals in FIG. 16. For some applications, one or more electrodes 470 are positioned so as to define a closest electrode distance D3 to a longitudinal central axis 502 of tissue 476 that is at least approximately 1 mm. Alternatively or additionally, one or more electrodes 470 are positioned such that D3 is at least approximately 1.1, 1.5, or 2 times a radius D4 of tissue 476. For some applications, a surface 504 of at least one end insulating element 474 that is in physical contact with tissue 476 is configured so as to promote connective tissue growth between tissue 476 and the surface. Such connective tissue growth generally supports the insulating contact between the insulating element and tissue 476. For example, so as to promote the connective tissue growth:

- surface 504 may be rough;
- surface 504 may be treated with a growth factor that promotes the connective tissue growth, such as TGF-beta 1 or TGF-beta 2;
- talc may be applied to surface 504 (talc is a known stimulator of fibrosis); and/or
- a material structure, such as a plastic mesh, may be applied to surface 504.

In an embodiment of the present invention, outer wall 478 and/or external surfaces of insulating elements 474 of cuff 500 are configured to promote the growth of a fibrosis sleeve around cuff 500. Such a fibrosis sleeve generally insulates the internal environment of cuff 500 from the surrounding external environment, for example so as to reduce current leakage from the cuff. Techniques for promoting fibrous connective tissue growth may be used that are described hereinabove with reference to surface 504.

Reference is now made to FIG. 18, which is a schematic, cross-sectional illustration of a cuff 520, in accordance with an embodiment of the present invention. Numerals in FIG. 18 refer to the same elements as corresponding numerals in FIGS. 16 and 17. In the embodiment shown in FIG. 18, end insulating elements 474 are configured so as to define a tissue surface axial distance A1 between longitudinal sites on tissue 476 at which the insulating elements are in physical contact with the tissue. Distance A1 is less than an electrode surface axial length A2 of electrode 470 that is in electrical contact with the tissue. Such a configuration provides a relatively high current density through the surface area of tissue 476 between the insulating elements, while allowing for a relatively high electrode capacitance (which depends on the surface area of the electrode). In an embodiment, A2 is between about 1.5 and about 5 times A1. The surface area of the electrode is also greater than the surface area of tissue 476 between the insulating elements because closest electrode distance D3 is greater than radius D4 of tissue 476 (FIG. 17). For example, the surface area of the electrode may be between about 1.05 and about 4 times the surface area of tissue 476 between the insulating elements, or between about 4 and about 10 times the surface area of tissue 476 between the insulating elements. Although end insulating elements 474 are shown as having a generally linear shape, for some applications the end insulating elements have other shapes, such as curved shapes.

Figure 19:
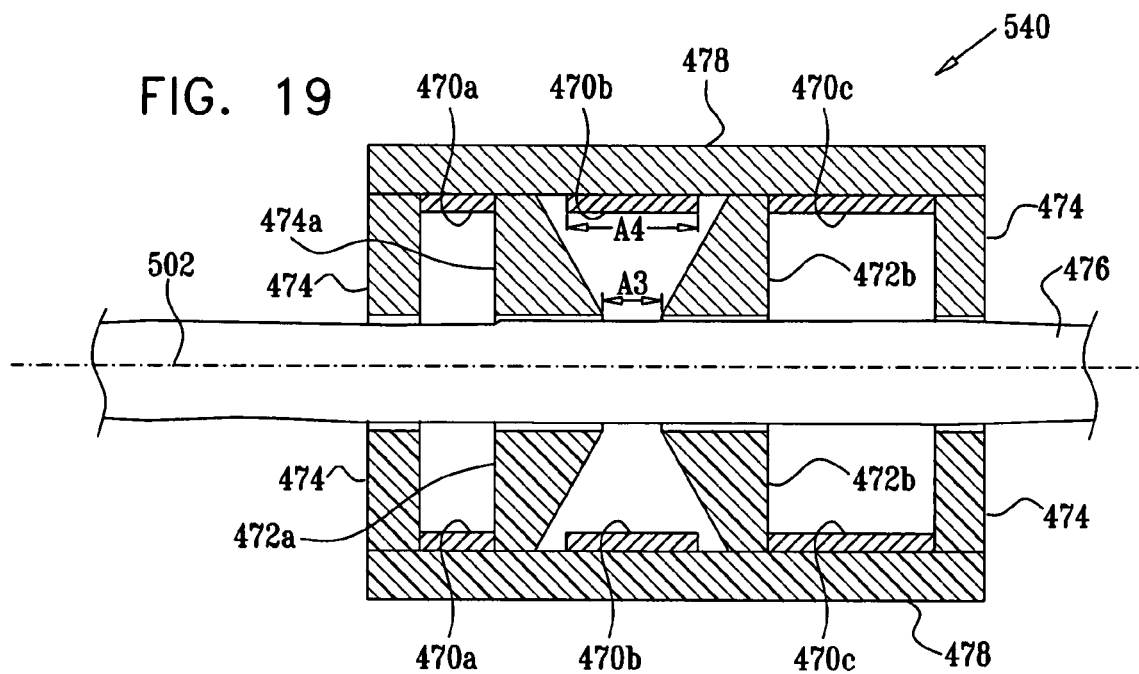

Reference is now made to FIG. 19, which is a schematic, cross-sectional illustration of a cuff 540, in accordance with an embodiment of the present invention. Numerals in FIG. 19 refer to the same elements as corresponding numerals in FIGS. 16, 17, and 18. Cuff 540 comprises (a) electrodes 470a, 470b, and 470c, and (b) first and second internal insulating elements 472a and 472b, which are positioned between electrodes 470a and 470b, and between electrodes 470b and 470c, respectively, and which are typically adapted to be in physical contact with tissue 476 after placement of the cuff. Internal insulating elements 472a and 472b are configured so as to define a tissue surface axial distance A3 between longitudinal sites on tissue 476 at which the insulating elements are in physical contact with the tissue. Distance A3 is less than an electrode surface axial length A4 of electrode 470b that is in electrical contact with the tissue. In an embodiment, A4 is between about 1.5 and about 5 times A3. The surface area of electrode 470b is also greater than the surface area of tissue 476 between internal insulating elements 472a and 472b, because a closest electrode distance to longitudinal central axis 502 of tissue 476 is greater than a radius of tissue 476. For example, the surface area of electrode 470b may be between about 1.05 and about 4 times the surface area of tissue 476 between internal insulating elements 472a and 472b. Alternatively, the surface area of electrode 470b may be between about 4 and about 110 times the surface area of tissue 476 between internal insulating elements 472a and 472b. Although internal insulating elements 472a and 472b are shown as having a generally linear shape, for some applications the internal insulating elements have other shapes, such as curved shapes.

In an embodiment of the present invention, an anti-fibrosis agent is applied to one or more electrode surfaces in order to prevent fibrosis growth in a vicinity of the surfaces. For example, the anti-fibrosis agent may include FG-3019, Penicillamine, Colchicine, or potassium amino-benzoate.

Figure 20:
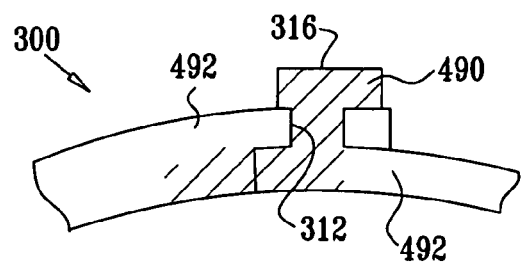
FIG. 20 is an enlarged cross-sectional view of a portion of the cuff of FIGS. 8 and 9 in a closed position, in accordance with an embodiment of the present invention.

FIG. 20 is an enlarged cross-sectional view of tubular cuff 300 in a closed position, in accordance with an embodiment of the present invention. Shaded area 490 may comprise material having a greater hardness than that of the material of non-shaded areas 492. Alternatively, head portion 316 may comprise a material that is softer than some or all of the material used elsewhere on cuff 300, particularly surrounding hole 312.

Although the techniques described hereinabove with reference to FIGS. 15, 16, and 20 are described with respect to cuff 300, these techniques are also applicable to cuffs 400, 500, 520, and 540, mutatis mutandis.

In an experiment conducted by the inventors, an electrode cuff similar to cuff 400 was implanted around a vagus nerve of a dog. After one month, the cuff showed no signs of tearing or coming loose from the nerve.

FIGS. 21-24 are graphs modeling calculated activation functions over a portion of the length of nerve 30, when current is applied using a tripolar ring electrode assembly similar to that shown in FIG. 2A (without applying current through anodes 74, 76, and 80), in accordance with an embodiment of the present invention. Anodes 78 and 72 are driven to apply currents A1=0.5 and A2=0.5, respectively. For the purposes of modeling the activation functions, each of the electrodes is assumed to have a longitudinal width of 1 and a radius of 1, and nerve 30 is assumed to have a radius of 1. Each of the electrodes generates its own activation functions responsive to the applied currents, as modeled in FIGS. 21-24.

The top data line in FIGS. 21-24 shows that the cathode generates a depolarization portion surrounded by two smaller hyperpolarization portions. The second and third data lines in FIGS. 21-24 show that each of the anodes generates a hyperpolarization portion surrounded by two smaller depolarization portions. The bottom data line in FIGS. 21-24 shows the combined effect on the total activation function, due to the cathodic activation function and the anodal activation functions.

Figure 21:
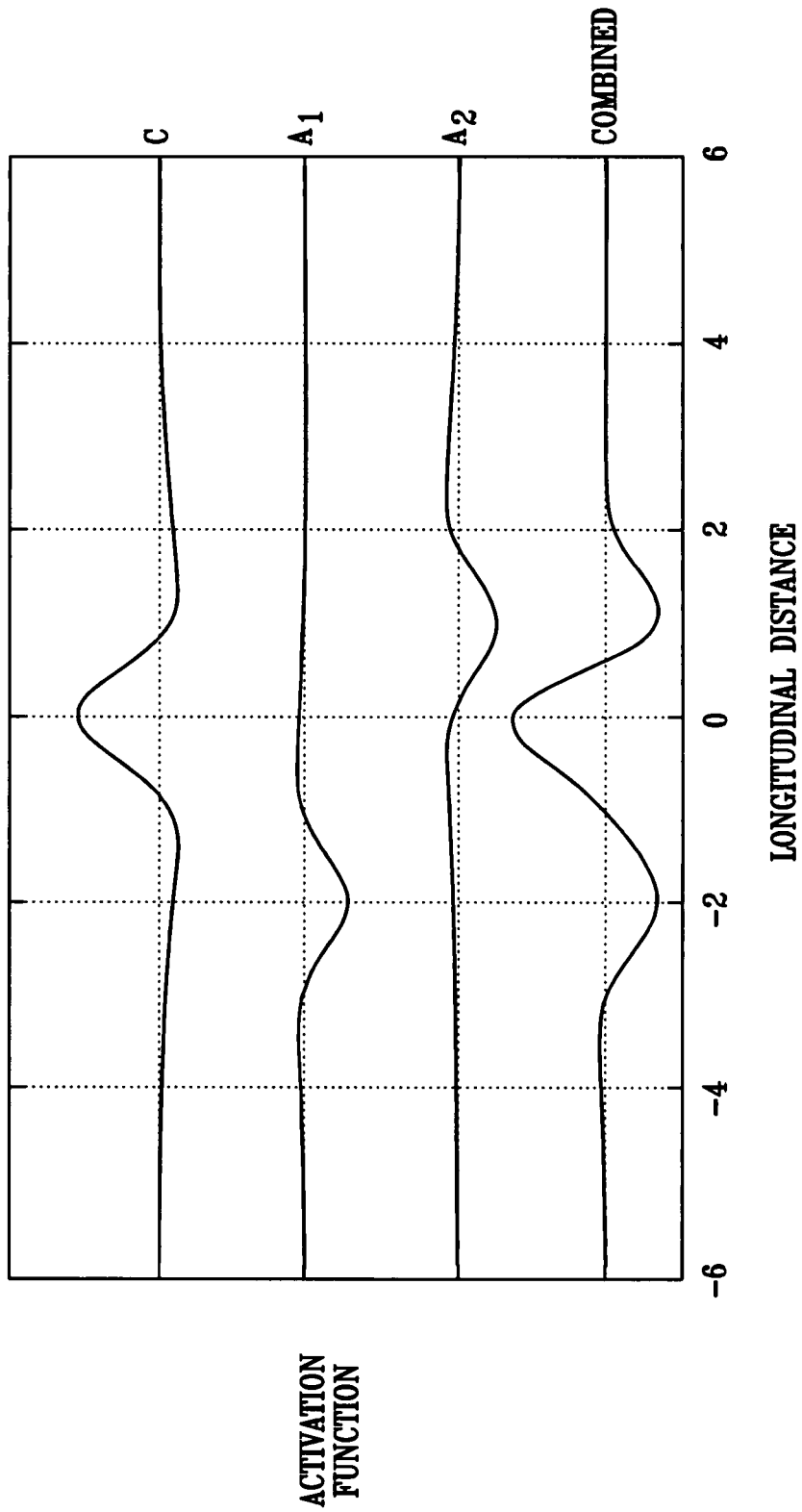
FIGS. 21-24 are graphs modeling calculated activation functions over a portion of the length of a nerve, when current is applied using a tripolar ring electrode assembly similar to that shown in FIG. 2A, in accordance with an embodiment of the present invention.
Figure 22:
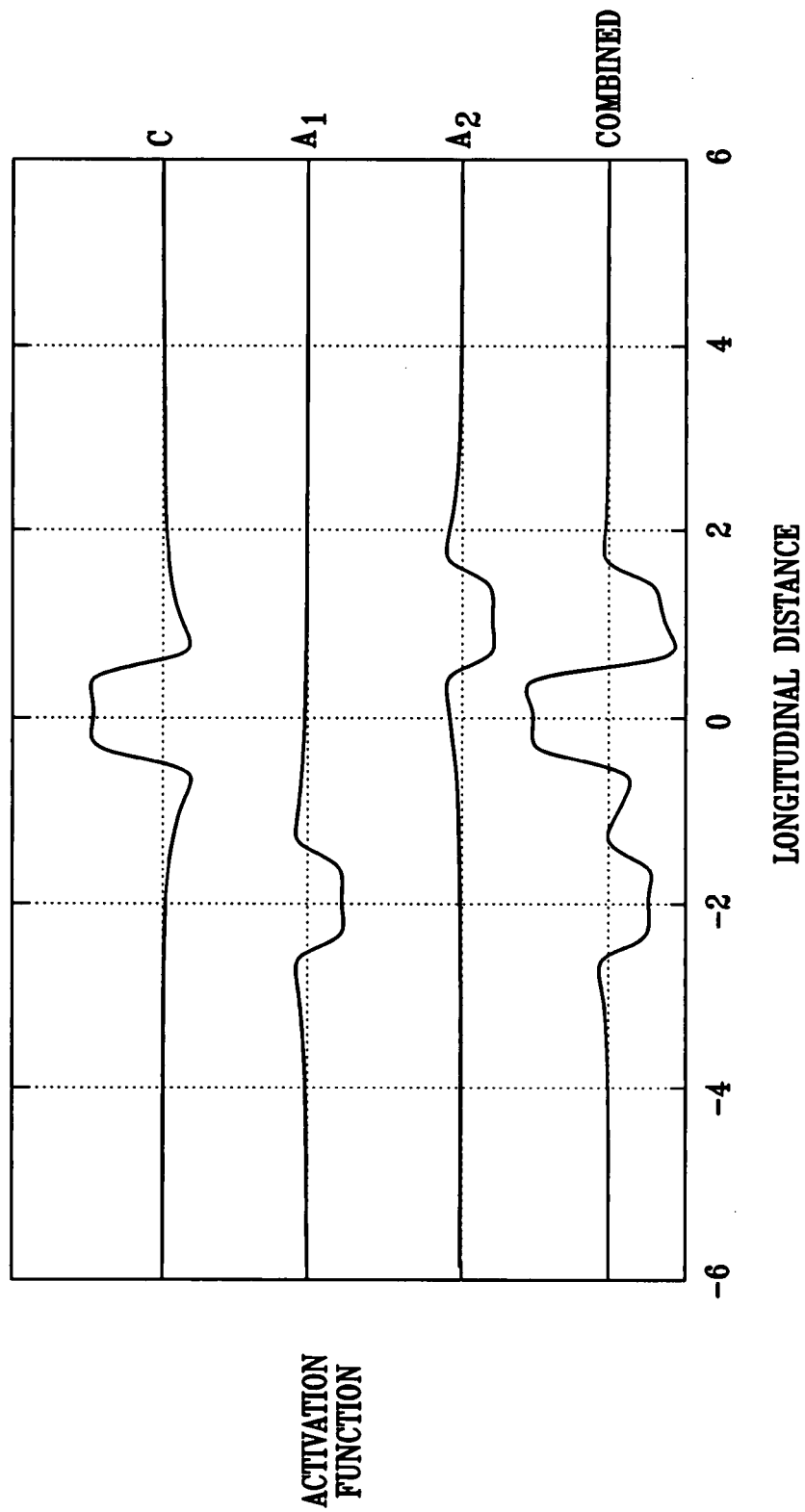

Reference is now made to FIGS. 21 and 22. For the purposes of modeling the activation functions shown in these figures, cathode 70 is placed at a longitudinal site on the nerve labeled z=0 (in relative units), and anodes 78 and 72 are placed at longitudinal positions z=−2 and 1, respectively. The cathode and anodes are placed at a radius of R=1 from the axis of nerve 30. FIG. 21 shows a modeled activation function at a radius R=0 from the axis of nerve 30 (i.e., at the axis of the nerve), and FIG. 22 shows a modeled activation function at R=0.8. Each of the combined activation functions has two hyperpolarization peaks, at approximately z=−2 and z=1, corresponding to the longitudinal positions of the two anodes. As can be seen in the graphs, at R=0, the left and right hyperpolarization peaks of the combined activation function have similar amplitudes (FIG. 21), while at R=0.8, the left and right hyperpolarization peaks of the combined activation function have substantially different amplitudes (FIG. 22).

Figure 23:
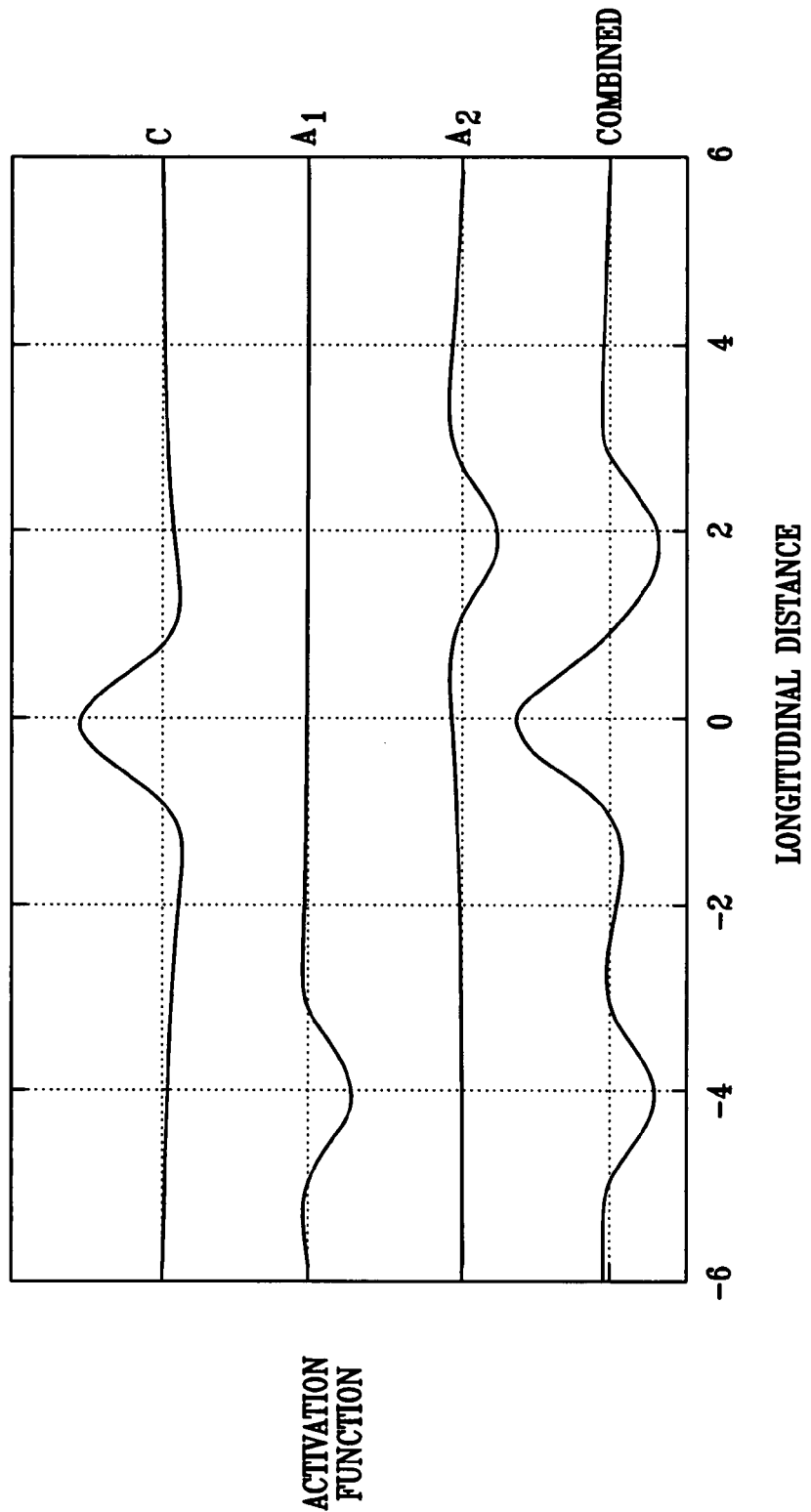
Figure 24:
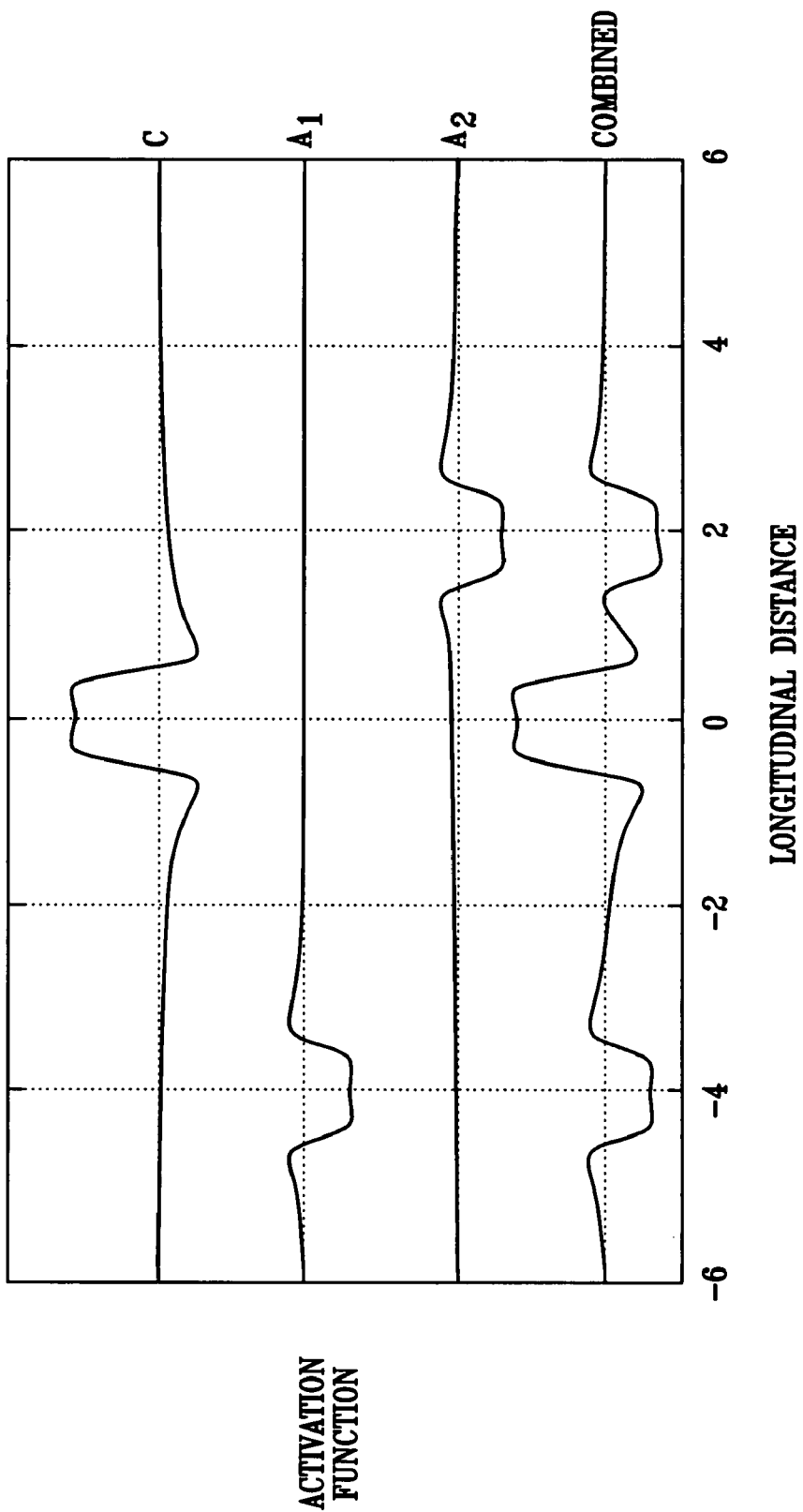

Reference is now made to FIGS. 23 and 24. For the purposes of modeling the activation functions shown in these figures, cathode 70 is placed at a longitudinal site on the nerve labeled z=0 (in relative units), and anodes 78 and 72 are placed at longitudinal positions z=−4 and 2, respectively. Again, the cathode and anodes are placed at R=1. FIGS. 23 and 24 show modeled activation functions at R=0 and R=0.8, respectively. Each of the combined activation functions has two hyperpolarization peaks, at approximately z=−4 and z=2, corresponding to the longitudinal positions of the two anodes. As can be seen in the graphs, at both R=0 and R=0.8, the left and right hyperpolarization peaks of the combined activation function have similar amplitudes.

Unlike the typical anode positioning of FIGS. 21 and 22, the increased distances between the anodes and the cathode of the simulations of FIGS. 23 and 24 result in ratios of left to right hyperpolarization peaks that do not vary substantially at different radii from the nerve axis. Typically, at these increased anode-to-cathode distances, the longitudinal regions of the nerve hyperpolarized by both of the anodes are at a sufficient distance from the cathode so as to not overlap with the regions hyperpolarized by the cathode. In contrast, at the typical closer distances shown in FIGS. 21 and 22, for some radii, the longitudinal region of the nerve hyperpolarized by one of the anodes overlaps with one of the regions hyperpolarized by the cathode (at about z=0.75 in FIG. 22), resulting in a hyperpolarization peak at this region which is greater than the hyperpolarization peak at the longitudinal region of the other anode.

Figure 25:
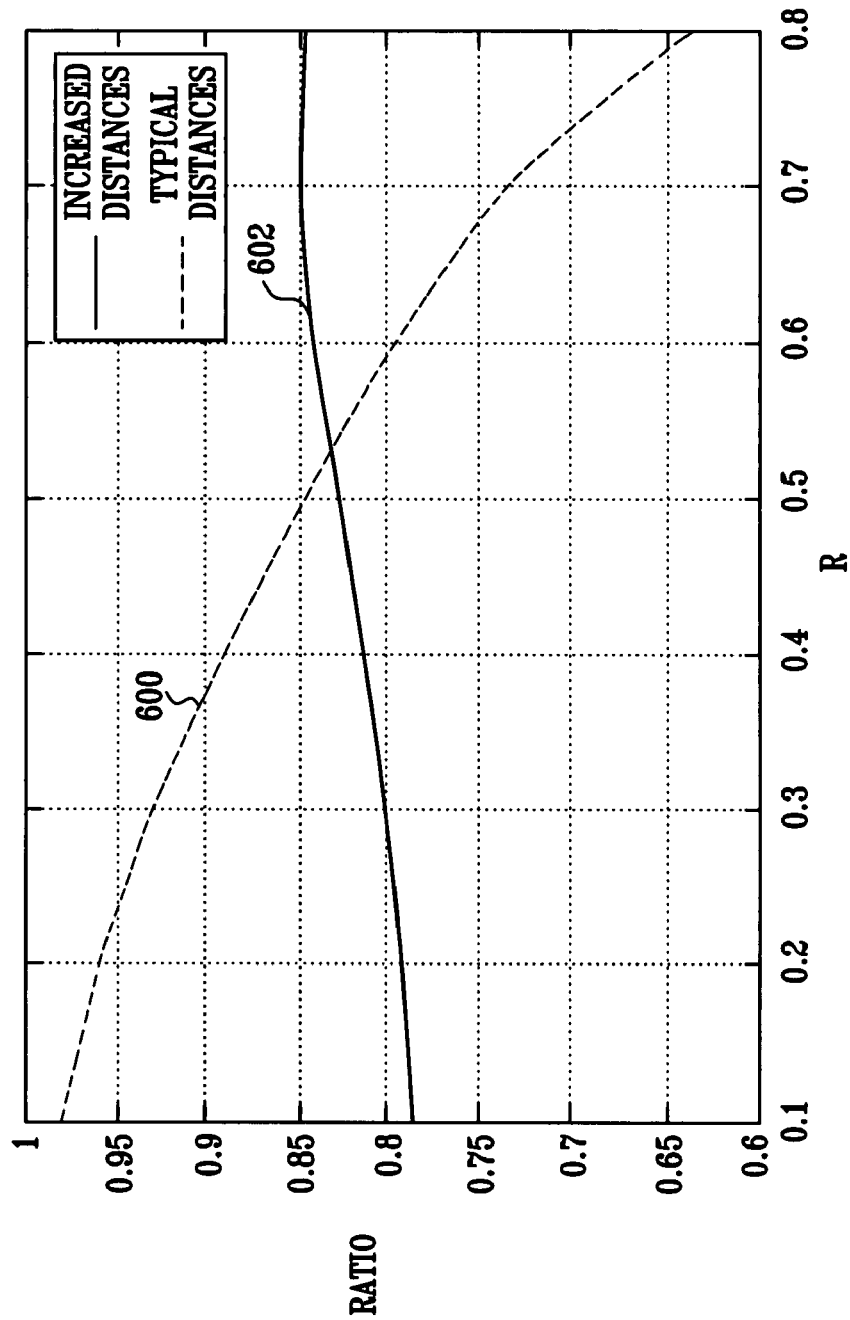
FIG. 25 is a graph showing the ratios of peak hyperpolarization amplitudes at left and right anodal longitudinal regions, at several radii, based on modeled calculated activation functions, in accordance with an embodiment of the present invention.

FIG. 25 is a graph showing the ratios of peak hyperpolarization amplitudes at left and right anodal longitudinal regions, at several radii R, based on modeled calculated activation functions using the parameters described hereinabove with reference to FIGS. 21-24, in accordance with an embodiment of the present invention. A data line 600 shows these ratios for the electrode configuration of FIGS. 21 and 22, in which the anodes are at typical distances from the cathode. A data line 602 shows these ratios for the electrode configuration of FIGS. 23 and 24, in which at least one of the anodes is at an increased distance from the cathode. As can be seen in the graph, the ratios for the increased anode-to-cathode distance configuration (line 602) vary substantially less than do the ratios for the typical distance configuration (line 600).

Figure 26:
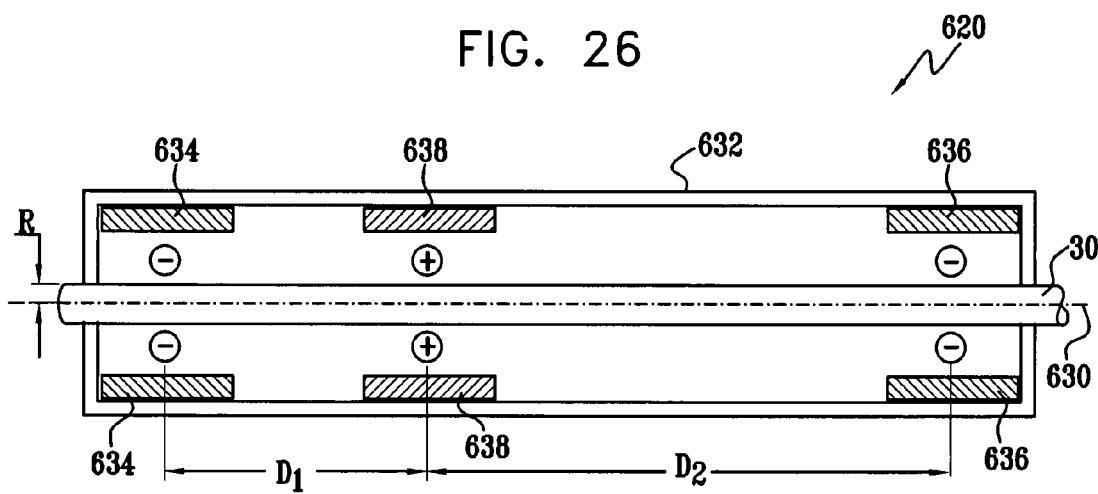
FIG. 26 is a schematic, cross-sectional illustration of another electrode assembly for applying current to a nerve, in accordance with an embodiment of the present invention.

Reference is made to FIG. 26, which is a schematic, cross-sectional illustration of an electrode assembly 620 for applying current to a nerve 30, in accordance with an embodiment of the present invention. Except as described hereinbelow, electrode assembly 620 is generally similar to electrode assembly 20, described hereinabove with references to FIGS. 1A and 1B. Nerve 30 has a radius R and a longitudinal central axis 630. Electrode assembly 620 comprises a housing 632, adapted to be placed in a vicinity of nerve 30; a first anode 634 and a second anode 636, fixed to housing 632; and a cathode 638, fixed to housing 632 between first and second anodes 634 and 636.

For some applications, a first distance D1 between a longitudinal center of first anode 634 and a longitudinal center of cathode 638, and a second distance D2 between a longitudinal center of second anode 636 and a longitudinal center of cathode 638 are each at least 1 times, e.g., at least 1.5 times or at least 2 times, the radius R of nerve 30.

Figure 27:
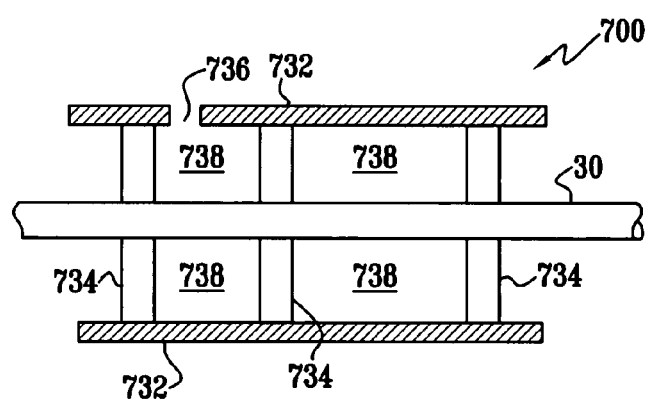
FIG. 27 is a schematic, cross-sectional illustration of yet another electrode assembly for applying current to a nerve, in accordance with an embodiment of the present invention.

FIG. 27 is a schematic, cross-sectional illustration of an electrode assembly 700 for applying current to nerve 30, in accordance with an embodiment of the present invention. Electrode assembly 700 comprises a housing 732, and one or more electrodes 734 fixed to the housing. Typically, housing 732 and electrodes 734 form a complete circle around nerve 30. Alternatively, the housing and/or electrodes define an arc between approximately 0 and 90 degrees, between 90 and 180 degrees, between 180 and 350 degrees, or between 350 and 359 degrees around the nerve. For some applications, electrodes 734 are fixed to housing 732 so as to define a closest electrode distance to the surface of nerve 30 that is less than about 0.5 mm. For example, one or more of electrodes 734 may be in direct physical contact with nerve 30 when electrode assembly 700 is applied to the nerve.

Housing 732 is shaped so as to define an outer surface having one or more holes 736 therethrough, such that biological materials and body fluids can pass through the holes into chambers 738 defined by nerve 30, housing 732, and electrodes 734 and/or insulating elements (insulating elements not shown). Typically, the outer surface is shaped so as to define holes 736 into only one of chambers 738, so as to avoid current leakage between anodal and cathodic chambers. After implantation of electrode assembly 700, fibrosis tissue typically grows in chambers 738, thereby providing electrical insulation within the chambers.

It is noted that housings and insulating elements shown in a number of the figures effectively define one or more chambers. FIGS. 17 and 18, for example, each show one chamber, whose borders are defined by outer wall 478, electrode 470, end insulating elements 474, and tissue 476. FIG. 19 shows three chambers, which are typically largely or completely electrically isolated from each other. FIG. 2A shows six interconnected chambers.

The chambers shown in the figures typically surround at least 180 degrees of the tissue enclosed within the housing, and, for most applications, extend substantially completely around the tissue. In this manner, the current applied to the tissue at any given longitudinal location is generally circumferentially symmetrical. This is true whether the tissue is (a) completely surrounded by a single electrode (e.g., a ring electrode), (b) mostly surrounded by an electrode (e.g., a C-shaped electrode), or (c) in effect surrounded by an electrode, by having disposed therearound a plurality of smaller electrodes (e.g., "point" electrodes or small planar electrodes).

Alternatively, none of the chambers surrounds greater than 180 degrees of the tissue. For example, two or more mutually electrically-isolated chambers may surround the tissue at a given longitudinal location of the tissue. In this case, the applied current is typically configured such that at any one longitudinal location of the tissue, the current applied thereto is substantially circumferentially symmetrical. For example: (a) a single ring electrode may apply a substantially circumferentially-symmetric current to the tissue, interrupted to a small extent at barriers between the chambers (e.g., insulating elements), or (b) a plurality of point electrodes or larger electrodes disposed around the tissue in multiple chambers may drive a current through the tissue towards one or more electrodes disposed at a different longitudinal location of the tissue.

In some embodiments, a single point electrode, in a single chamber that substantially surrounds the tissue, produces a substantially circumferentially symmetric application of current to the tissue. In the absence of insulating elements at the longitudinal location of the point electrode, the electrical potential at the longitudinal location, within the housing and outside of the tissue, is substantially homogenous, because the contents of this region have relatively low impedance. Therefore, for example, when a current is driven between point electrodes disposed at two respective longitudinal locations of the tissue, each point electrode being within its own chamber and each chamber surrounding substantially 360 degrees of the tissue, the effective current application to the tissue is substantially circumferentially symmetric at each of the longitudinal locations.

It will be appreciated that whereas ring electrodes are typically described in the present patent application, any electrode or application of current described in the specification or recited in the claims may be embodied in a single electrode, or in a plurality of electrodes held at substantially the same electrical potential. Thus, for example, an anode described as being at a particular location may be embodied as a single discrete anode, or as a plurality of anodes which together drive anodic current through tissue to a cathode. Similarly, a cathode described as being at a particular location may be embodied as a single discrete cathode, or as a plurality of cathodes which together drive cathodic current through tissue to an anode.

By contrast to the substantially circumferentially symmetric application of current to tissue, as described, techniques described herein may be adapted to drive current through tissue in a circumferentially asymmetric fashion, for example, by driving current between two sites at the same longitudinal location of the tissue (e.g., (a) from 12 o'clock to 3 o'clock, (b) from 12 o'clock to 6 o'clock, or (c) from the region spanning 12 o'clock to 2 o'clock to the region spanning 4 o'clock to 6 o'clock).

As appropriate, techniques described herein are practiced in conjunction with methods and apparatus described in one or more of the following applications which are assigned to the assignee of the present patent application and incorporated herein by reference:

U.S. Pat. No. 6,907,295 to Gross et al., entitled, "Electrode assembly for nerve control,"

PCT Patent Application PCT/IL03/00430, filed May 23, 2003, entitled, "Electrode assembly for nerve control," and U.S. patent application Ser. No. 10/529,149 in the US national stage thereof U.S. patent application Ser. No. 10/205,475 to Gross et al., filed Jul. 24, 2002, entitled, "Selective nerve fiber stimulation for treating heart conditions,"

U.S. Provisional Patent Application 60/383,157 to Ayal et al., filed May 23, 2002, entitled, "Inverse recruitment for autonomic nerve systems,"

PCT Patent Application PCT/IL02/00068 to Cohen et al., filed Jan. 23, 2002, entitled, "Treatment of disorders by unidirectional nerve stimulation,"

U.S. patent application Ser. No. 09/944,913 to Cohen and Gross, filed Aug. 31, 2001, entitled, "Treatment of disorders by unidirectional nerve stimulation," which issued as U.S. Pat. No. 6,684,105 to Cohen et al., U.S. patent application Ser. No. 09/824,682 to Cohen and Ayal, filed Apr. 4, 2001, entitled "Method and apparatus for selective control of nerve fibers," and U.S. patent application Ser. No. 10/205,475 to Gross et al., filed Jul. 24, 2002, entitled, "Selective nerve fiber stimulation for treating heart conditions."

It will thus be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for applying current to a nerve, comprising an electrode assembly, which comprises:
   a housing, adapted to be placed completely around the nerve, the housing shaped so as to define an outer surface and a plurality of chambers, including first and second chambers, that define respective open spaces between the housing and the nerve when the housing is placed around the nerve;
   one or more electrodes, fixed to the housing, which electrodes comprise an anode and a cathode, one of which is fixed to the housing within the first chamber, and the other of which is fixed to the housing within the second chamber; and
   a control unit, which is configured to drive a cathodic current through the cathode, and an anodal current through the anode,
   wherein the electrode assembly is shaped so as to define a plurality of openings through which the nerve passes when the housing is placed around the nerve, and
   wherein, in addition to the openings of the electrode assembly through which the nerve passes, the outer surface of the housing is shaped so as to define one or more holes through to the first chamber, and no holes through to the second chamber, which holes through to the first chamber are configured to allow passage of biological materials therethrough to the first chamber.

2. The apparatus according to claim 1, wherein the outer surface is shaped so as to define the one or more holes into only the first chamber.

3. A method comprising:
   providing an electrode assembly including (a) a housing shaped so as to define an outer surface and (b) one or more electrodes, fixed to the housing; and
   placing the housing completely around a nerve, such that the housing defines a plurality of chambers, including first and second chambers, that define respective open spaces between the housing and the nerve, and the electrode assembly defines a plurality of openings through which the nerve passes, wherein, in addition to the openings of electrode assembly through which the nerve passes, the outer surface of the housing is shaped so as to define one or more holes through to the first chamber, and no holes through to the second chamber, which holes through to the first chamber are configured to allow passage of biological materials therethrough to the first chamber, wherein the electrodes include an anode and a cathode, one of which is fixed to the housing within the first chamber, and the other of which is fixed to the housing within the second chamber, and further comprising driving a cathodic current through the cathode, and an anodal current through the anode.

4. The method according to claim 3, wherein providing the electrode assembly comprises providing the electrode assembly in which the outer surface is shaped so as to define the one or more holes into only the first chamber.

* * * * *